(12) United States Patent
Huibregtse et al.

(10) Patent No.: US 10,012,598 B2
(45) Date of Patent: Jul. 3, 2018

(54) MULTI-WAVELENGTH LASER CHECK DETECTION TOOL

(71) Applicant: Emhart Glass S.A., Cham (CH)

(72) Inventors: David Huibregtse, Palm Bay, FL (US); Scott L. French, Pinellas Park, FL (US)

(73) Assignee: Emhart S.A., Cham (CH)

( * ) Notice: Subject to any disclaimer, the term of this patent is extended or adjusted under 35 U.S.C. 154(b) by 0 days.

(21) Appl. No.: 15/194,088

(22) Filed: Jun. 27, 2016

(65) Prior Publication Data

US 2017/0016833 A1      Jan. 19, 2017

Related U.S. Application Data

(60) Provisional application No. 62/193,863, filed on Jul. 17, 2015.

(51) Int. Cl.
| | |
|---|---|
| *G01N 21/00* | (2006.01) |
| *G01N 21/90* | (2006.01) |
| G01N 21/88 | (2006.01) |

(52) U.S. Cl.
CPC ..... *G01N 21/9036* (2013.01); *G01N 21/9054* (2013.01); *G01N 2021/8845* (2013.01); *G01N 2201/06113* (2013.01)

(58) Field of Classification Search
CPC ........ G01N 21/47; G01N 21/64; G01N 21/90; G01N 21/88; G01N 21/958; G01N 21/6428; G01N 21/9036; G01N 21/9054; G01N 21/9045; G01N 2021/8845; G01N 2201/06113; G01N 15/02
See application file for complete search history.

(56) References Cited

U.S. PATENT DOCUMENTS

| | | | |
|---|---|---|---|
| 3,302,786 A | * | 2/1967 | Conrad ................. G01N 21/90 |
| | | | 209/526 |
| 3,533,704 A | | 10/1970 | Krenmayer |
| 3,684,385 A | | 8/1972 | Einfalt et al. |
| 3,877,821 A | | 4/1975 | Price et al. |
| 3,880,750 A | | 4/1975 | Butler et al. |
| 3,963,918 A | | 6/1976 | Jensen et al. |

(Continued)

FOREIGN PATENT DOCUMENTS

| | | |
|---|---|---|
| DE | 2411723 A1 | 9/1975 |
| DE | 3815539 A1 | 11/1989 |

(Continued)

*Primary Examiner* — Jamil Ahmed
(74) *Attorney, Agent, or Firm* — Reinhart Boerner Van Deuren P.C.

(57) ABSTRACT

A device and method for inspecting glass containers and particularly the finish of glass containers is provided. The glass container inspection device includes a rotator rotates a glass container located in an inspection location at least 360 degrees. A first laser source produces a first laser beam which is directed towards the inspection location to form an angle of incidence with the selected glass container being greater than or equal to a critical angle for producing internal reflection of the first laser beam within the selected glass container. A camera is directed at the inspection location to detect light that escapes from the selected glass container as a result of the internally reflected laser beam intersecting a defect in the selected glass container.

38 Claims, 15 Drawing Sheets

(56) References Cited

U.S. PATENT DOCUMENTS

| | | |
|---|---|---|
| 3,991,883 A | 11/1976 | Hobler et al. |
| 4,175,236 A | 11/1979 | Juvinall |
| 4,201,338 A | 5/1980 | Keller |
| 4,213,042 A | 7/1980 | Beach et al. |
| 4,213,702 A | 7/1980 | Bryant et al. |
| 4,230,266 A | 10/1980 | Juvinall |
| 4,249,075 A | 2/1981 | Lovalenti |
| 4,476,533 A | 10/1984 | Daudt et al. |
| 4,644,151 A | 2/1987 | Juvinall |
| 4,655,349 A | 4/1987 | Joseph et al. |
| 4,697,076 A | 9/1987 | Yoshida |
| 4,701,612 A | 10/1987 | Sturgill |
| 4,713,536 A | 12/1987 | Williams et al. |
| 4,811,251 A | 3/1989 | Minato |
| 4,816,668 A | 3/1989 | Williams et al. |
| 4,908,507 A | 3/1990 | Imre et al. |
| 4,929,828 A | 5/1990 | Claypool |
| 4,945,228 A | 7/1990 | Juvinall et al. |
| 4,958,223 A | 9/1990 | Juvinall et al. |
| 4,967,070 A | 10/1990 | Ringlien et al. |
| 4,990,792 A | 2/1991 | Frei |
| 5,020,908 A | 6/1991 | Hermann |
| 5,028,769 A | 7/1991 | Claypool et al. |
| 5,175,428 A | 12/1992 | Agerskov et al. |
| 5,200,801 A | 4/1993 | Juvinall et al. |
| 5,249,034 A | 9/1993 | Minato |
| 5,489,987 A | 2/1996 | Ringlien |
| 5,617,204 A | 4/1997 | Hinata |
| 5,895,911 A | 4/1999 | Giometti et al. |
| 5,896,195 A | 4/1999 | Juvinall et al. |
| 5,900,945 A | 5/1999 | Hinata et al. |
| 6,025,909 A | 2/2000 | Juvinall et al. |
| 6,104,482 A | 8/2000 | Brower et al. |
| 6,172,748 B1 | 1/2001 | Sones |
| 6,175,107 B1 | 1/2001 | Juvinall |
| 6,211,952 B1 | 4/2001 | Weiland et al. |
| 6,239,869 B1 | 5/2001 | Heuft et al. |
| 6,256,095 B1 | 7/2001 | Ringlien |
| 6,275,287 B1 | 8/2001 | Watanabe |
| 6,448,549 B1 | 9/2002 | Safaee-Rad |
| 6,480,280 B1 | 11/2002 | Hinata |
| 6,549,288 B1 | 4/2003 | Migdal et al. |
| 6,549,292 B1 | 4/2003 | Schmidt et al. |
| 6,621,569 B2 | 9/2003 | Sones |
| 6,903,814 B1 | 6/2005 | Juvinall et al. |
| 7,005,629 B2 | 2/2006 | Flem |
| 7,060,999 B2 | 6/2006 | Juvinall |
| 7,148,961 B1 | 12/2006 | Ringlien |
| 7,317,524 B2 | 1/2008 | Gerard et al. |
| 7,329,855 B2 | 2/2008 | Katayama et al. |
| 7,414,716 B2 | 8/2008 | Sones et al. |
| 7,417,725 B2 | 8/2008 | Colle et al. |
| 7,541,572 B2 | 6/2009 | Novini et al. |
| 7,582,856 B2 | 9/2009 | Weber et al. |
| 7,626,158 B2 | 12/2009 | Diehr et al. |
| 7,697,132 B2 | 4/2010 | Sones et al. |
| 7,815,539 B2 | 10/2010 | Ward et al. |
| 7,816,639 B2 | 10/2010 | Diehr et al. |
| 7,876,951 B2 | 1/2011 | Novini et al. |
| 8,548,771 B2 | 10/2013 | Holden et al. |
| 8,941,825 B2 | 1/2015 | Juvinall et al. |
| 9,147,241 B2 | 9/2015 | Numazu |
| 9,194,814 B2 | 11/2015 | Numazu |
| 9,322,787 B1 | 4/2016 | Huibregtse et al. |
| 9,329,135 B2 | 5/2016 | Diehr et al. |
| 9,562,860 B1 * | 2/2017 | Pangarkar .......... G01N 21/6428 |
| 2003/0112430 A1 | 6/2003 | Lindner |

FOREIGN PATENT DOCUMENTS

| | | |
|---|---|---|
| EP | 0234105 A1 | 9/1987 |
| JP | 56110006 A | 9/1981 |
| JP | H07103915 A | 4/1995 |

* cited by examiner

MULTI-WAVELENGTH LASER CHECK DETECTION TOOL

CROSS-REFERENCE TO RELATED PATENT APPLICATIONS

This patent application claims the benefit of U.S. Provisional Patent Application No. 62/193,863, filed Jul. 17, 2015, the entire teachings and disclosure of which are incorporated herein by reference thereto.

FIELD OF THE INVENTION

This invention generally relates to machines that inspect glass containers for defects.

BACKGROUND OF THE INVENTION

In the glass container industry, small cracks or fracture in the glass are referred to as "check defects". Checks can range from sub millimeters to several hundred millimeters and can be oriented at any direction from vertical to horizontal. Glass is not a crystalline structure by nature, but most cracks propagate roughly along a plane of some orientation in space mostly determined by the shape of the glass at that location. For example, a crack that began as a vertical crack at the upper surface of the mouth primarily propagates in a vertical plane. Checks can appear in any orientation and on any portion of a container and can exist wholly within the glass or may penetrate to one or both surfaces. Checks are considered phase objects and do not absorb light like a solid objects does. Checks are primarily reflective in nature if their opposed surface separation is at least half a wavelength of light. However, very few checks with a smaller separation will reflect light and accordingly they will not likely be detectable by direct reflection methods, but they might have scattering points when they penetrate to the one or both surfaces of the container and will scatter light back to the sensors.

Most of these crack defects will drastically weaken the bottle, often causing it to rupture or to leak. Therefore, bottle manufactures like to remove these containers before they reach filling plants. Checks appearing near the mouth of the containers are called finish checks. In the glass bottle industry, the term "container finish" refers to the portion of the bottle that defines the mouth, threads or beads, and the ring. The upper surface of the mouth is referred as the sealing surface.

Almost all commercially available check detectors work on the principle of reflected light. A conventional check detector consists of a series of continuously operating light spot light sources and associated photodetectors that are positioned so that known checks on a bottle rotating at an inspection station will reflect light from one of the sources to one of the photo-detectors. Signal processing of the photodetector outputs recovers the sharp peaks while rejecting lower frequency signal variations caused by ambient light, reflection from the bottle sidewall, threads, etc.

While commercially available check detectors are successfully deployed on most glass bottle production lines, there are several drawbacks to the approach. A few of those are: many point sensors are required for many possible reflection angles; some sensor angles are difficult to position; additional sensors and lights need to be added as more production defects appear; time consuming setup is required for each type of container; and the difficulty of reproducing the same setup from one inspection line to another.

The following U.S. Pat. Nos. 4,701,612; 4,945,228; 4,958,223; 5,020,908; 5,200,801; 5,895,911; 6,104,482; 6,211,952; 6,275,287 and 7,815,539 all relate to devices that detect defects in the finish of a container.

Embodiments of the present invention provide improvements over the current state of the art relating to check detection and particularly check detection for check defects within the finish of a glass container. However, this technique can be applied to the whole container inspection.

BRIEF SUMMARY OF THE INVENTION

In one aspect, the invention provides improved inspection of glass containers and more particularly improved check defect inspection of the finish region of glass containers. The improved inspection of the glass containers can be used to control systems for removing a glass container from a stream of glass containers such that only glass containers that pass the inspection remain.

In one embodiment, a glass container inspection device for inspecting a finish region of the glass container includes a rotator, a first laser source and a camera. The rotator is configured to rotate a selected glass container located in an inspection location at least 360 degrees. The first laser source is configured to produce a first laser beam. The first laser source is configured to direct the first laser beam towards the inspection location to form an angle of incidence with the selected glass container being greater than or equal to a critical angle for producing internal reflection of the first laser beam within the selected glass container. The camera is directed at the inspection location for detecting light that escapes from the selected glass container as a result of the internally reflected laser beam intersecting a defect in the selected glass container.

In one embodiment, the first laser source is a multi-wavelength laser source configured such that the first laser beam is a multi-wavelength laser beam. By providing a multi-wavelength laser source, a plurality of colors of glass can be inspected. The multi-wavelength laser source includes first, second and third wavelength laser sources. The first wavelength laser source is configured to produce a first wavelength laser beam of a first wavelength of light. The second wavelength laser source is configured to produce a second wavelength laser beam of a second wavelength of light different than the first wavelength of light. The third wavelength laser source is configured to produce a third wavelength laser beam of a third wavelength of light different than the first and second wavelengths of light. The multi-wavelength light source is configured to direct the multi-wavelength laser beam towards the inspection location at an angle of incidence greater than or equal to a critical angle for producing total internal reflection of at least one of the first, second and third wavelength laser beams of the multi-wavelength laser beam within the selected glass container.

In one embodiment, the first wavelength of light is between 440-490 nm, the second wavelength of light is between 495-570 nm and the third wavelength of light is between 620-750 nm.

In a more particular embodiment, the first wavelength of light is between 440-460 nm, the second wavelength of light is between 510-530 nm and the third wavelength of light is between 625-665 nm.

In one embodiment, the first laser source has an excitation source having a power value of between 5-150 milliwatts average power continuous wave and more preferably between 25-100 milliwatts average power continuous wave.

In one embodiment, the first laser source is operably located and oriented relative to the inspection location such that the first laser beam has a first dimension parallel to a first axis of between 20 and 60 millimeters and a second dimension along a second axis perpendicular to the first dimension and first axis of between 25 and 100 micrometers.

In one embodiment, the rotator rotates the selected glass container about a container axis of rotation. The first axis of the first laser beam is at an angle of between 0 and 15 degrees relative to the container axis of rotation in a plane orthogonal to a focus axis of the first laser beam.

In one embodiment, the device includes a glass container transport arrangement for transporting the selected glass container into the inspection location, configured for stopping the selected glass container within the inspection location for a predetermined period of time at which time the rotator rotates the selected glass container at least 360 degrees, and configured for transporting the selected bottle out of the inspection location.

In one embodiment, the rotator is configured to rotate the selected glass container at least 720 degrees while in the inspection location and preferably such that each portion of the glass container to be inspected passes by the camera at least once and more preferably at least twice.

In one embodiment, the first laser source is configured to direct the first laser beam towards the selected glass container at an angle of incidence of at least 65 degrees and less than 90 degrees.

In one embodiment, the camera defines a camera focus axis directed toward the inspection location. The camera focus axis extends angularly relative to a first laser focus axis of the first laser source along which the first laser beam travels at a camera-to-laser angle of between 15 and 41 degrees and more preferably between 17 and 32 degrees. The camera may be a line scan camera or an area array camera.

In one embodiment, the first laser source and the camera are spaced from the inspection location such that the camera focus axis and the first laser focus axis intersect an outer periphery of a glass container within the inspection location prior to intersecting when the camera focus axis and the first laser focus axis are viewed in a direction extending parallel to a container axis of rotation about which the selected glass container is rotated by the rotator.

In one embodiment, an alignment mechanism simultaneously adjusts a position of the first laser source and the camera parallel to a plane normal to a container axis of rotation about which the selected glass container is rotated by the rotator.

In one embodiment, an alignment guide is carried with the camera and the first laser source such that when the alignment mechanism adjusts the position of the first laser source and the camera. The alignment guide defines a pair of alignment lines extending at a right angle to one another in the plane normal. Both alignment lines are positioned tangent to an outer periphery of a selected glass container within the inspection location when viewed along the container axis of rotation to set a position of the alignment mechanism and particularly the camera and first laser source.

In one embodiment, the alignment guide includes an alignment camera. The alignment camera is positioned to view a selected glass container within the inspection location and the alignment lines, at least when, the alignment lines are both tangent to the outer periphery of the selected glass container. An alignment display is operably connected to alignment camera displaying an output of the alignment camera.

In one embodiment, the system includes first laser beam delivery optics. The first laser beam delivery optics include second and third laser source redirection structures. The second laser source redirection structure is optically interposed between the second laser source and the inspection location for redirecting the second wavelength laser beam produced by the second wavelength laser source along a first laser focus axis. The third wavelength laser source redirection structure optically interposed between the third wavelength laser source and the inspection location for redirecting the third wavelength laser beam produced by the third wavelength laser source along the first laser focus axis such that the first, second and third wavelength laser beams are coincident when they intersect an outer periphery of a selected glass container within the inspection location. Further embodiments may have the laser beams separated such as by a distance of 1 mm. Additionally multiple beams within each wavelength range may be provided.

In one embodiment, the second wavelength laser source redirection structure is made of a material that allows the first wavelength of light to pass therethrough and the second wavelength of light is reflected and the third laser source redirection structure is made of a material that allows the first and second wavelengths of light to pass therethrough and the third wavelength of light is reflected.

In one embodiment, a first laser source redirection structure is optically interposed between the first laser source and the inspection location for redirecting the first wavelength laser beam produced by the first wavelength laser source along the first laser focus axis.

The laser source redirection structures may also be configured to shape the first, second and third wavelength laser beams such that they have substantially the same size and shape at the location of intersection with the outer periphery of the glass container.

In one embodiment, the first laser beam of the first laser source travels along a first laser focus axis as the first laser beam contacts an outer periphery of the selected glass container. A second laser source is also provided. The second laser source is configured to produce a second laser beam traveling along a second laser focus axis different than the first laser focus axis, the second laser source being configured to direct the second laser beam towards the selected glass container in the inspection location at a second angle of incidence with the selected glass container being greater than or equal to a critical angle for producing internal reflection of the second laser beam within the selected glass container. The second laser focus axis is at a skew angle relative to a plane normal to a container axis of rotation about which the rotator rotates the selected glass container. The second laser focus axis is offset from and not coaxial with the first laser focus axis.

In one embodiment, the second laser focus axis is directed to intersect an inside of an opening of the selected glass container such that horizontal defects can be detected using the camera or a second camera offset from the camera.

Methods of inspecting the finish region of the glass container are also provided. In some embodiments, the methods will utilize embodiments of devices as described above.

In a particular method, the method includes: rotating a selected glass container located in an inspection location at least 360 degrees; producing a first laser beam with a first laser source; directing the first laser beam towards the inspection location at an angle of incidence with the selected glass container being greater than or equal to a critical angle for producing internal reflection of the first laser beam within the selected glass container; and detecting light that escapes from the selected glass container as a result of the internally reflected laser beam intersecting a defect in the selected glass container.

In a particular method, producing the first laser beam includes producing a multi-wavelength laser beam and the first laser source is a multi-wavelength laser source including a first, second and third wavelength laser source. Producing the multi-wavelength laser beam includes: producing a first wavelength laser beam of a first wavelength of light with the first wavelength laser source; producing a second wavelength laser beam of a second wavelength of light different than the first wavelength of light with the second wavelength laser source; and producing a third wavelength laser beam of a third wavelength of light different than the first and second wavelengths of light with the third wavelength laser source. Directing the first laser beam includes directing the multi-wavelength laser beam towards the inspection location at an angle of incidence greater than or equal to a critical angle for producing total internal reflection of at least one of the first, second and third wavelength laser beams of the multi-wavelength laser beam within the selected glass container.

In one embodiment, the first wavelength of light is between 440-490 nm, the second wavelength of light is between 495-570 nm and the third wavelength of light is between 620-750 nm.

In one embodiment, the first wavelength of light is between 440-460 nm, the second wavelength of light is between 510-530 nm and the third wavelength of light is between 625-665 nm.

In one embodiment, the first laser source has an excitation source having a power value of between 5-150 milliwatts average power continuous wave and more preferably between 25-100 milliwatts average power continuous wave.

In one embodiment, the first laser beam has a first dimension parallel to a first axis of between 20 and 60 millimeters and a second dimension along a second axis perpendicular to the first dimension and first axis of between 25 and 100 micrometers. These dimensions are generally perpendicular to the focus axis along which the laser beam propagates.

In one embodiment, rotating the selected glass container includes rotating the selected glass container about a container axis of rotation. The first axis of the first laser beam is at an angle of between 0 and 15 degrees relative to the container axis of rotation in a plane orthogonal to a focus axis of the first laser beam.

In one embodiment, a method includes transporting the selected glass container into the inspection location; stopping the selected glass container within the inspection location for a predetermined period of time during which the step of rotating the selected glass container occurs while the selected glass container is stopped within the inspection location; and transporting the selected bottle out of the inspection location.

In one method, rotating includes rotating the selected glass container at least 720 degrees while in the inspection location.

In one method, directing the first laser beam includes directing the first laser beam towards the selected glass container at an angle of incidence of at least 65 degrees and less than 90 degrees.

In one method, detecting light that escapes from the selected glass container is performed using camera defining a camera focus axis directed toward the inspection location. The camera focus axis extends angularly relative to a first laser focus axis of the first laser source along which the first laser beam travels at a camera-to-laser angle of between 17 and 32 degrees. The camera may be line scan camera or an area array camera.

In one method, the first laser source and the camera are spaced from the inspection location such that the camera focus axis and the first laser focus axis intersect an outer periphery of a glass container within the inspection location prior to intersecting one another when the camera focus axis and the first laser focus axis are viewed in a direction extending parallel to a container axis of rotation about which the selected glass container is rotated by the rotator.

In one method, the method includes adjusting, simultaneously, a position of the first laser source and a camera for detecting light that escapes parallel to a plane normal to a container axis of rotation about which the selected glass container is rotated.

In one method, adjusting the position of the first laser source and the camera includes using an alignment guide being carried with the camera and the first laser source when the position of the first laser source and the camera is adjusted. The alignment guide defines a pair of alignment lines extending at a right angle to one another in the plane normal. Adjusting the position includes aligning both alignment lines tangent to an outer periphery of a selected glass container within the inspection location when viewed along the container axis of rotation to set a position of the alignment mechanism.

In one method, adjusting the position of the first laser source and the camera includes viewing a selected glass container within the inspection location and the alignment lines with an alignment camera and an alignment display operably connected to alignment camera displaying an output of the alignment camera.

In one method, directing the multi-wavelength laser beam includes using first laser beam delivery optics. Using the first laser beam optics includes redirecting, with a second laser source redirection structure optically interposed between the second laser source and the inspection location, the second wavelength laser beam produced by the second wavelength laser source along a first laser focus axis; redirecting, with a third wavelength laser source redirection structure optically interposed between the third wavelength laser source and the inspection location, the third wavelength laser beam produced by the third wavelength laser source along the first laser focus axis such that the first, second and third wavelength laser beams are coincident when they intersect an outer periphery of a selected glass container within the inspection location.

In one method, the second wavelength laser source redirection structure is made of a material that allows the first wavelength of light to pass therethrough and the second wavelength of light is reflected and the third laser source redirection structure is made of a material that allows the first and second wavelengths of light to pass therethrough and the third wavelength of light is reflected.

In one method, the method includes redirecting, with a first laser source redirection structure optically interposed between the first laser source and the inspection location, the first wavelength laser beam produced by the first wavelength laser source along the first laser focus axis.

In one method, directing the first laser beam includes directing the first laser beam of the first laser source along a first laser focus axis as the first laser beam contacts an outer periphery of the selected glass container. The method further includes producing a second laser beam, with a second laser source, traveling along a second laser focus axis different than the first laser focus axis; and directing the second laser beam towards the selected glass container in the inspection location at a second angle of incidence with the selected glass container being greater than or equal to a critical angle for producing internal reflection of the second laser beam within the selected glass container, the second laser focus axis being at a skew angle relative to a plane normal to a container axis of rotation about which the rotator rotates the selected glass container.

In one method, directing the second laser beam directs the second laser beam such that the second laser focus axis is directed to intersect an inside surface of an opening of the selected glass container such that horizontal defects are detected. In an embodiment, defects identified by the first laser beam are detected with a first camera and defects identified by the second laser beam are detected with a second camera.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
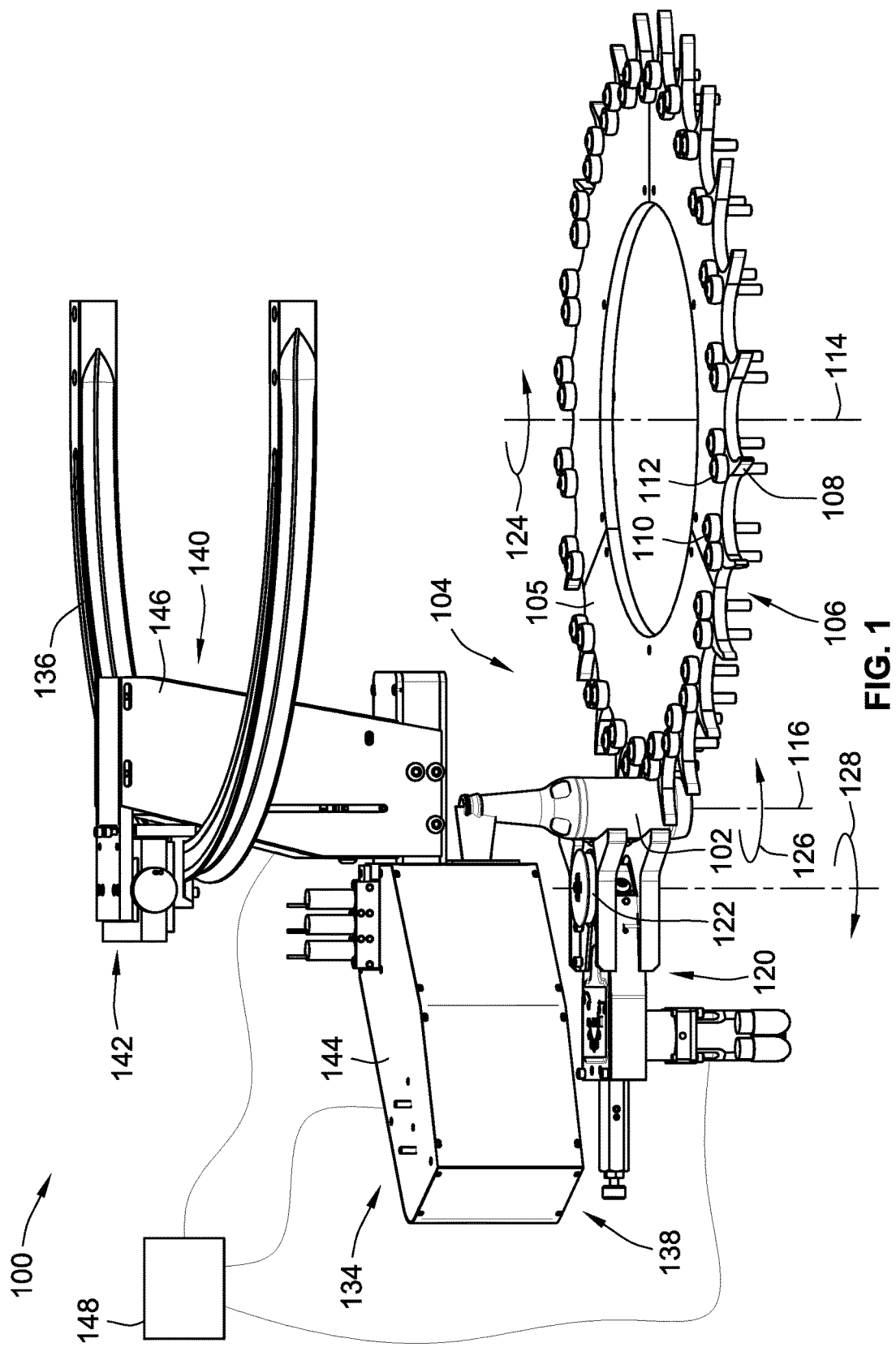
FIG. 1 is a simplified illustration of glass container inspection device according to an embodiment of the present invention.

An embodiment of glass container inspection device 100 is illustrated in FIG. 1. The glass container inspection device 100 uses one or more lasers directed at a glass container 102 to inspect the glass container for check defects (also referred to as "anomalies" or simply "defects") in the glass container 102. The glass container inspection device 100 is configured, particularly, to inspect the finish region of the glass container 102 (also referred to as "the finish").

While only a single glass container 102 is illustrated throughout the illustrations, it will be understood that the glass container 102 is one of many in a stream of glass containers that will be fed to the glass container inspection device 100. Typically, the stream of glass containers 102 will be supplied to and taken away from the glass container inspection device by one or more conveyors (not shown).

The glass container inspection device 100 generally defines an inspection location where glass containers will be inspected for defects. In FIG. 1, glass container 102 is located in the inspection location and is being inspected.

The glass container inspection device 100 of the illustrated embodiment includes a glass container transport arrangement 104 for transporting the glass containers 102 into the inspection location. Once the glass container 102 is in the inspection location, the glass container transport arrangement maintains the glass container 102 within the inspection location for a predetermined period of time. In some embodiments, the predetermined period of time may be as short as 125 milliseconds and is typically about 150 milliseconds. Due to the speed and volume of glass containers 102 being inspected, the period of time will typically be less than 500 milliseconds, but longer time periods could be used. At this time, the glass container 102 is inspected for defects. After the inspection is complete, the glass container transport arrangement 104 transports the glass container 102 out of the inspection location and generally out of the glass container inspection device 100. The glass containers 102 may be placed on a new conveyor, back onto the conveyor that supplied the bottles to the glass container inspection device 100 or otherwise released to travel to downstream processes.

Thereafter, if the glass container 102 is found to include a significant enough defect, the glass container 102 will be removed from the stream of glass containers using known systems and devices for separating the defective glass container from the otherwise acceptable glass containers. Typically, these glass containers will be destroyed and then recycled and the glass thereof will be reformed into new glass containers.

If the glass container passes the inspection and is not found to have any defects, the glass container 102 will travel to further processing which may include additional inspection processes.

In the illustrated embodiment, the glass container transport arrangement 104 includes a carousel 105 defining a plurality of pockets 106 sized and configured to guide an individual glass container 102 as it travels into, through and out of the inspection location. In this embodiment, the carousel 105 includes a plurality of pockets 106. The carousel 105 includes hook-shaped radially outward extending projections 108 that separate adjacent pockets 106. Each pocket 106 has a plurality of casters 110, 112 rotatably mounted to the carousel 105 proximate the pockets 106 such that a portion of the casters 110, 112 extend into a corresponding one of the pockets 106 to support a given glass container 102 when carried therein.

The carousel 105 is operably rotated about a carousel axis of rotation 114 to transport the glass containers 102 into, through and out of the inspection location. In the illustrated embodiment, the rotation of the carousel 105 is not constant. Instead, the rotation starts and stops such that, at least in part, the glass containers 102 do not move angularly about carousel axis of rotation 114 while being inspected. As such, the glass container transport arrangement 104 provides an indexing motion to the stream of containers as containers passes through the inspection location. While not shown, the glass containers 102 may be supported by a table, a conveyor, or other surface as the containers 102 are transported into, through, and out of the inspection location.

However, even though the glass container 102 may not move angularly about the carousel axis of rotation while being inspected within the inspection location, the glass container 102 rotates about a container axis of rotation 116 that is generally offset from and parallel to the carousel axis of rotation.

A rotator 120 is positioned adjacent the carousel 105 such that as a glass container 102 is transported into and held within the inspection location by the carousel, the outer periphery of the glass container 102 is in contact with one or more rotating drive wheels 122 of the rotator 120. The rotating drive wheels 122 of the rotator 120 and the casters 110, 112 are generally on opposed sides of the pocket 106 of the carousel such that the glass container 102 is supported, generally, on one side by the rotating drive wheels 122 and on the opposite side by the casters 110, 112.

So that the entire finish of the glass container 102 is inspected, the rotator 120 is configured to rotate the glass container 102 at least 360 degrees about the container axis of rotation 116 during the predetermined period of time at which it is positioned within the inspection location. In a preferred embodiment, the container 102 is rotated approximately 2.5 times (e.g. 900 degrees) while it is held within the inspection location for the above identified predetermined period of time. While the inspection by the glass container inspection device 100 is occurring, the carousel 105 is generally stationary such that the glass container 102 is not being angularly driven about the carousel axis of rotation 114 by carousel 105 to provide the indexing style of motion.

In the illustrated embodiment, the carousel 105 is driven in a counterclockwise direction illustrated by arrow 124 in FIG. 1. The rotator 120 is configured to rotate the glass container 102 in the counterclockwise direction illustrated by arrow 126. This rotation is accomplished by the rotating drive wheels 122 of the rotator 120 about an axis of rotation in the opposite, clockwise direction illustrated by arrow 128.

It should be noted that while the glass container 102 is being controlled by the glass container transport arrangement 104 it may be passed through other inspection systems for other inspections to be performed. These other inspections may occur upstream or downstream of the inspections of embodiments of the present invention.

The glass container inspection device 100 includes an optical inspection system 134 that is used to inspect the glass container 102 and, in the illustrated embodiment, the finish portion of the glass container 102. The optical inspection system 134 is mounted to a C-shaped mounting track 136 vertically above the rotator 120 and the carousel 105.

The optical inspection system 134 includes a first inspection arrangement 138 and a second inspection arrangement 140 which are operably mechanically connected together and are moved in unison relative to the mounting track 136 by mounting arrangement 142 as well as corresponding structural framework of the optical inspection system. Preferably, the mounting arrangement 142 allows for three-dimensional adjustment of the position of the optical inspection system 134 so as to adjust the position of the optical inspection system 134 to accommodate glass containers of different sizes and shapes. The first and second inspection arrangements 138, 140 are operably mounted to mounting track 136 by mounting arrangement 142 which clamps onto the mounting track 136. The mounting arrangement 142 may include adjustment mechanisms for individually adjusting the position of optical inspection system 134 in all three dimensions, such as for adjustment along all three axes of a Cartesian coordinate system.

While only optical inspection system 134 is illustrated mounted to mounting track 136, other inspection devices can be mounted thereto to perform additional inspections of the glass container 102 as it is indexed while under control of carousel 105.

The first and second inspection arrangements 138, 140 utilize lasers and a camera (also referred to as a receiver), to analyze the quality of the finish of the glass container 102. In FIG. 1, the lasers and camera are located within first and second housings 144, 146 of the first inspection arrangement 138 and second inspection arrangement 140, respectively. A controller 148 is operably connected to the optical inspection system 134 for controlling the lasers and camera as well as receiving feedback information from the lasers and camera and particularly from the camera. The controller 148 may operably connected to the rotator 120 and container transport arrangement 104 for operable control thereof, i.e. for adjusting rotation speeds and timing for properly controlling the motion of the glass containers. Further, the controller 148 may be configured to selectively activate and deactivate any one of the lasers, control laser power levels as well as the camera.

Figure 2:
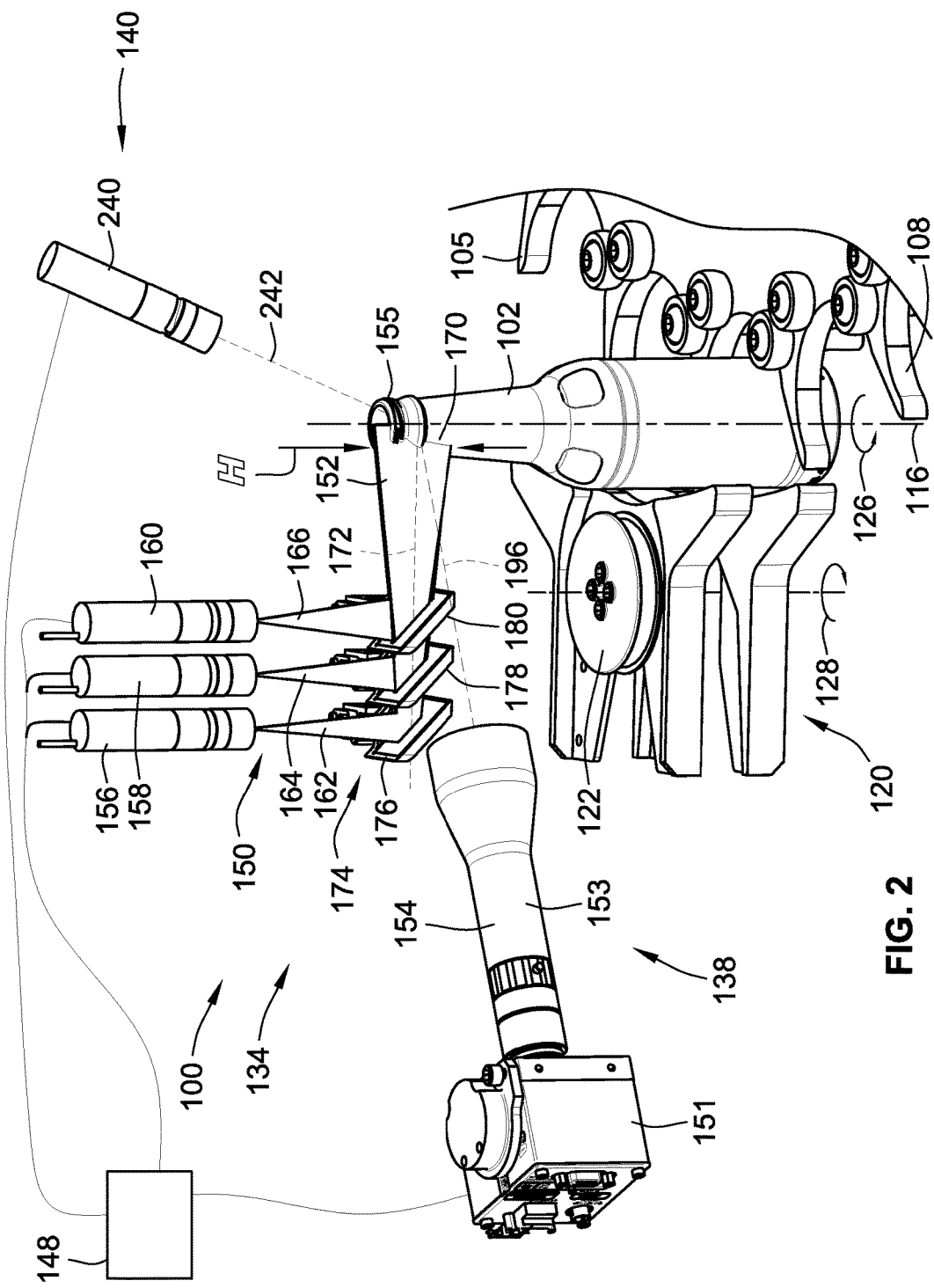
FIG. 2 is a simplified partial illustration of the glass container inspection device of FIG. 1 illustrating the optical inspection system thereof.

FIG. 2 is a simplified illustration of the glass container inspection device 100 of FIG. 1. This illustration has housings 144, 146 removed to illustrate the components of the glass container inspection device 100 that perform the inspection of the glass container 102 while located within the inspection location. More particularly, components of the optical inspection system 134 are illustrated.

Among other things, the first inspection arrangement 138 of the optical inspection system 134 includes a first laser source 150 configured to produce a first laser beam 152 that is directed towards inspection location and particularly the glass container 102 within the inspection location. The first laser beam 152, as will be described more fully below, is directed towards the inspection location and particularly the glass container 102 such that at least one wavelength of light forming the laser beam 152 enters the sidewall 155 of the glass container 102. The sidewall 155 functions as a waveguide that totally internally reflects the wavelength of light unless the light encounters a defect in the glass at which time it is reflected out of the glass of the glass container 102. The first laser source 150 is generally used to identify vertically oriented defects or at least defects that have a vertically oriented component. The orientation and configuration of the first laser source 150 is such that the light that enters the sidewall 155 of the glass container can experience the total internal reflection identified above.

A camera 154 is oriented and directed towards the inspection location and particularly the glass container 102 to sense light that is reflected out of the glass container 102 due to the presence of a defect in the glass which inhibits the ability for total internal reflection. The camera 154 includes a camera body 151 and a lens 153. The camera 154 may be in the form of a line-scan camera or an area array camera.

The first laser source 150 in the embodiment of FIG. 2 is a multi-wavelength laser source configured such that the first laser beam 152 is a multi-wavelength laser beam formed from a plurality of wavelengths of light. Preferably, the laser beam 152 is tophat or homogenous. More particularly, the first laser 150 source includes first, second and third wavelength laser sources 156, 158, 160. The first wavelength laser source 156 is configured to produce a first wavelength laser beam 162 of a first wavelength of light. The second wavelength laser source 158 is configured to produce a second wavelength laser beam 164 of a second wavelength of light. The third wavelength laser source 160 is configured to produce a third wavelength laser beam 166 of a third wavelength of light. The first, second and third wavelengths of light are used such that glass containers formed from different color glass can be inspected using the same first laser source 150.

In the illustrated embodiment, the three wavelengths of light are in the blue, green and red spectrums. More particularly, the first wavelength of light is between 440-490 nm and more preferably between 440-460 nm and even more preferably is 450 nm (blue), the second wavelength of light is between 495-570 nm and more preferably between 510-530 nm and even more preferably is 520 nm (green), and the third wavelength of light is between 620-750 nm, more preferably between 625-665 nm, more preferably between 630-650 nm and even more preferably is 640 nm (red). Again, by using different wavelengths of light a large variety of glass colors can be inspected. Depending on the color of the glass, a given wavelength of light may be reflected or absorbed rather than transmitted through the glass via total internal reflection as used in the instant embodiment.

A benefit in the use of lasers rather than other light sources such as LED's is that a laser provides a coherent collimated light that is substantially monochromatic providing only a single wavelength of light. This allows the light, e.g. first laser beam 152, to be precisely directed toward the outer periphery 170 of the glass container 102 so that the light can enter the sidewall 155 in a precise location and the glass container 102 can function as a waveguide to permit total internal reflection of the light.

The first laser source 150 is configured so that the first, second and third wavelength laser beams 162, 164, 166 are operably aligned as they travel along a first laser focus axis 172 towards the inspection location and are substantially coincident with one another when they intersect the periphery 170 of the glass container 102.

Figure 3:
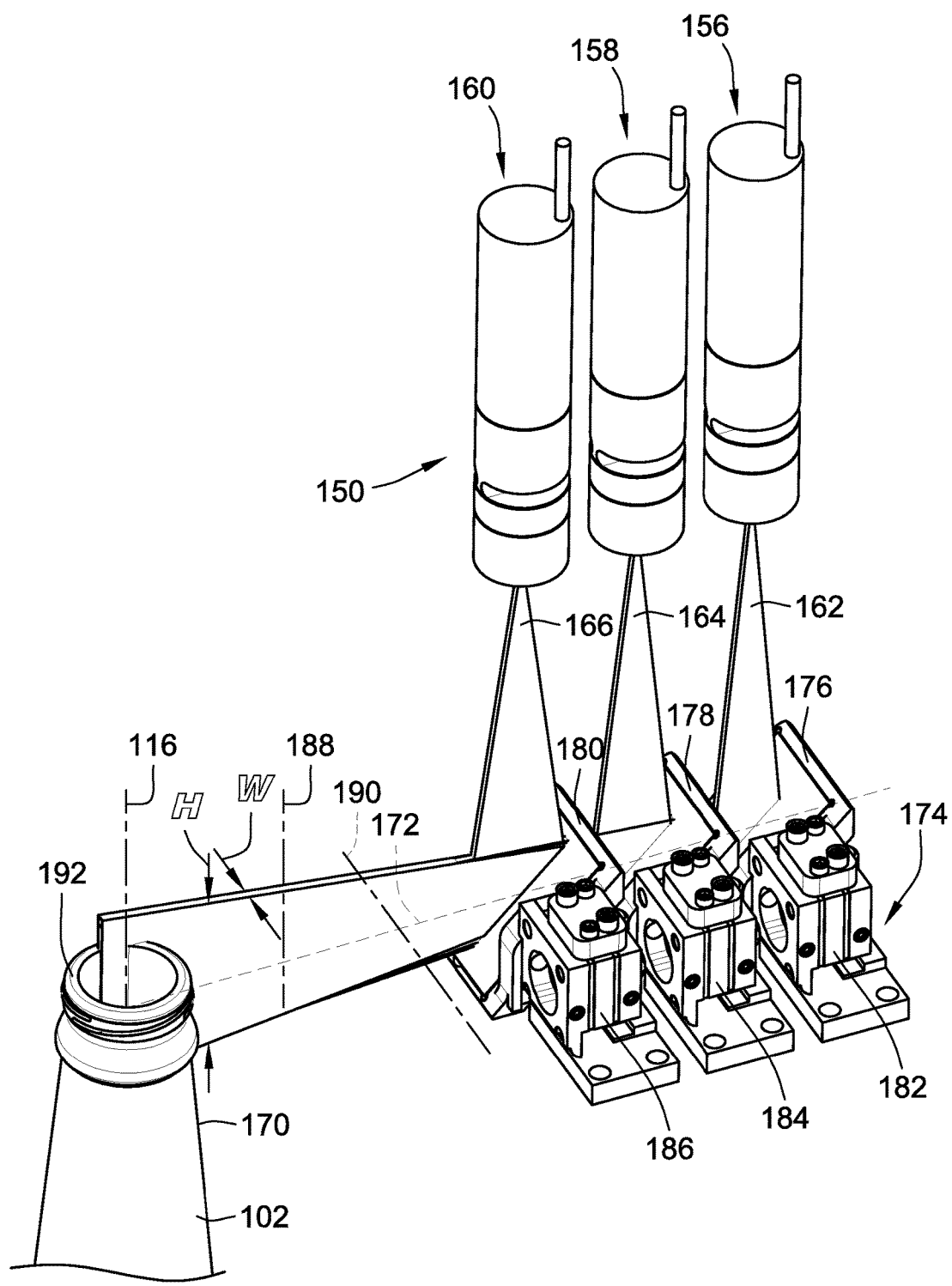
FIG. 3 is a partial illustration of the glass container inspection device illustrating a first inspection arrangement thereof.

With reference to FIGS. 2 and 3, to align the first, second and third wavelength laser beams 162, 164, the first laser source 150 includes laser beam delivery optics 174. In the illustrated embodiment, the laser beam delivery optics 174 include a first laser source redirection structure 176 optically interposed between the first wavelength laser source 156 and the inspection location. The first laser source redirection structure 176 changes the direction of the first wavelength laser beam 162 as the first wavelength laser source 156 is aligned off of the first laser focus axis 172. The first laser source redirection structure 176 also assists in calibrating the fan angle of the first wavelength laser beam 162 such that it is coincident with the second and third wavelength laser beams 164, 166 at the intersection point of the first laser beam 152 and the outer periphery 170 of the glass container 102.

The laser beam delivery optics 174 include a second laser source redirection structure 178 optically interposed between the second wavelength laser source 158 and the inspection location. The second laser source redirection structure 178 changes the direction of the second wavelength laser beam 164 as the second wavelength laser source 158 is aligned off of the first laser focus axis 172. The second laser source redirection structure 178 also assists in calibrating the fan angle of the second wavelength laser beam 164 such that it is coincident with the first and third wavelength laser beams 162, 166 at the intersection point of the first laser beam 152 and the outer periphery 170 of the glass container 102.

The laser beam delivery optics 174 include a third laser source redirection structure 180 optically interposed between the third wavelength laser source 160 and the inspection location. The third laser source redirection structure 180 changes the direction of the third wavelength laser beam 166 as the third wavelength laser source 160 is aligned off of the first laser focus axis 172. The third laser source redirection structure 180 also assists in calibrating the fan angle of the third wavelength laser beam 166 such that it is coincident with the first and second wavelength laser beams 162, 164 at the intersection point of the first laser beam 152 and the outer periphery 170 of the glass container 102.

In an embodiment, the second laser source redirection structure 178 is made of a material or otherwise mechanically configured such that it allows the first wavelength of light of the first wavelength laser beam 162 to pass therethrough. However, second laser source redirection structure 178 is made of a material or otherwise mechanically configured such that the second wavelength of light of the second wavelength laser beam 164 is reflected. Similarly, the third laser source redirection structure 180 is made of a material or otherwise mechanically configured such that it allows the first wavelength of light of the first wavelength laser beam 162 and the second wavelength of light of the second wavelength laser beam 164 to pass therethrough. However, the third laser source redirection structure 180 is made of a material or otherwise mechanically configured such that the third wavelength of light of the third wavelength laser beam 166 is reflected. In one embodiment, the first, second and third laser source redirection structures 174, 176, 178 are dichroic beamsplitters. The dichroic beamsplitters are configured to allow 98% of the wavelength(s) of light that is desired to pass therethrough to pass through the material while 98% of the of the wavelength of light that is desired to be reflected is reflected.

The use of these first, second and third laser source redirection structures 176, 178, 180 allows the first, second and third wavelength laser sources 156, 158, 160 to be located off of the first laser focus axis 172 but to then redirect the laser beams 162, 164, 166 thereof into a unified coherent and coincident multi-wavelength laser beam, e.g. the portion of laser beam 152 downstream from the third laser source redirection structure 180.

The first, second and third laser source redirection structures 176, 178, 180 are mounted to corresponding locking optical mounts 182, 184, 186 (see FIG. 3) that allow for adjusting the position and orientation of the laser source redirection structures 176, 178, 180 and that provide no movement over time or vibration. Once the laser source redirection structures 176, 178, 180 are properly aligned, the optical mounts 182, 184, 186 are locked.

Figure 4:
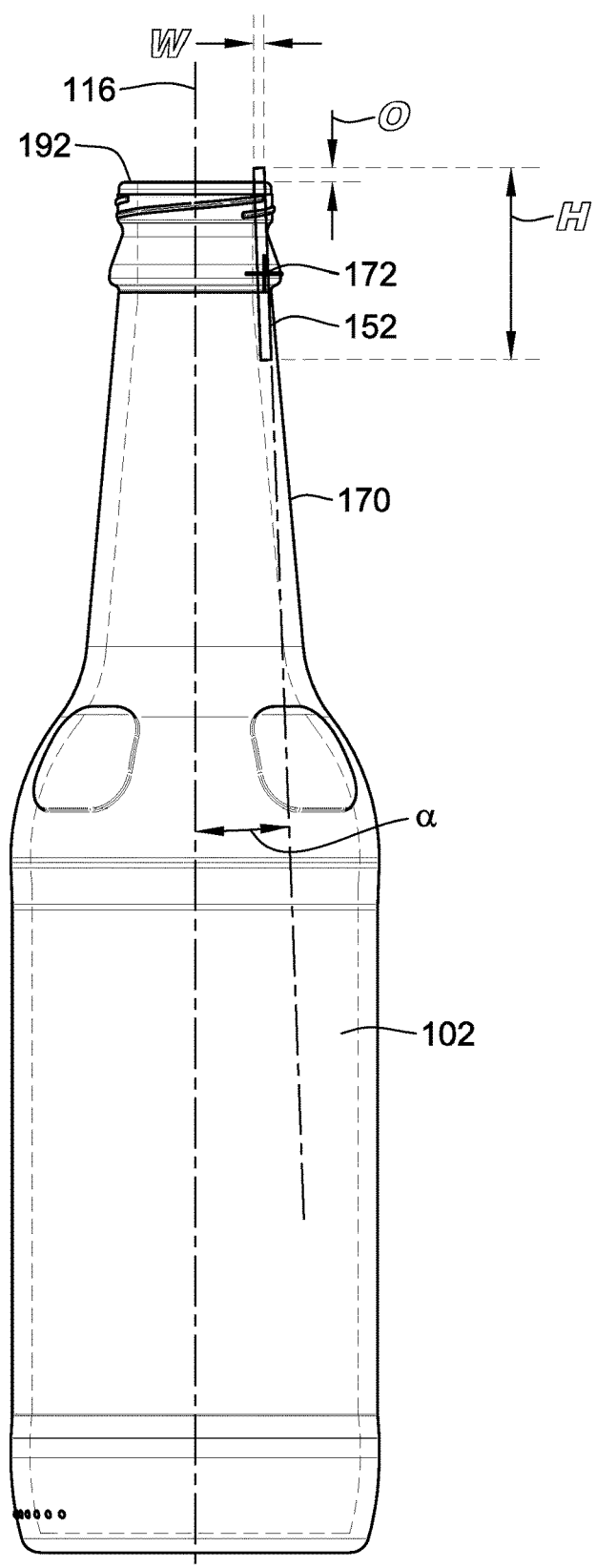
FIG. 4 illustrates a glass container being contacted by a laser beam of the first inspection arrangement of FIG. 3.

With reference to FIGS. 2-4, the first, second and third wavelength laser sources 156, 158, 160 in conjunction with the first, second and third laser source redirection structures 176, 178, 180 are operably configured and positioned relative to the inspection location and a glass container 102 such that the first laser beam 152 has a height H parallel to a first axis 188 that in this embodiment is parallel to vertical that is between 20 and 60 millimeters and is more preferably between 40 and 50 millimeters at the location where the laser beam 152 contacts the outer periphery 170 of the glass container 102. The first, second and third wavelength laser sources 156, 158, 160 in conjunction with the first, second and third laser source redirection structures 176, 178, 180 are operably configured and positioned relative to the inspection location and a glass container 102 such that the first laser beam 152 has a width W parallel to a second axis 190 that in this embodiment is parallel to second axis 190 and perpendicular to first axis 188 and the first laser focus axis 172 that is between 25 and 125 micrometers and more preferably between 50 and 100 micrometers. To make sure the entire vertical extent of the desire portion of the glass container 102 is being inspected e.g. the finish, in the illustrated embodiment, the first laser beam 152 is directed towards the glass container 102 such that a portion of the first laser beam 152 extends vertically above the sealing surface 192 of the finish of the glass container 102 by an offset distance O of approximately 3 millimeters.

Preferably, at least 95 percent of the entire cross-section of the first laser beam 152 that intersects the glass container 102 includes and is formed by all three wavelengths of light in an overlapped relationship.

In an embodiment, the first, second and third wavelength laser sources 156, 158, 160 have an excitation source that has a power value of between 5-150 milliwatts average power continuous wave and more preferably between 25-100 milliwatts average power continuous wave.

With reference to FIG. 4, a glass container 102 is illustrated with first laser beam 152. The first laser beam 152 forms an angle α with the axis of container axis of rotation 116 of approximately 0 degrees. However, in some embodiments, the value of angle α may range between −5 and 15 degrees. However other values are contemplated depending on the contour and shape of the portion of the glass container 102 being inspected.

Figure 5:
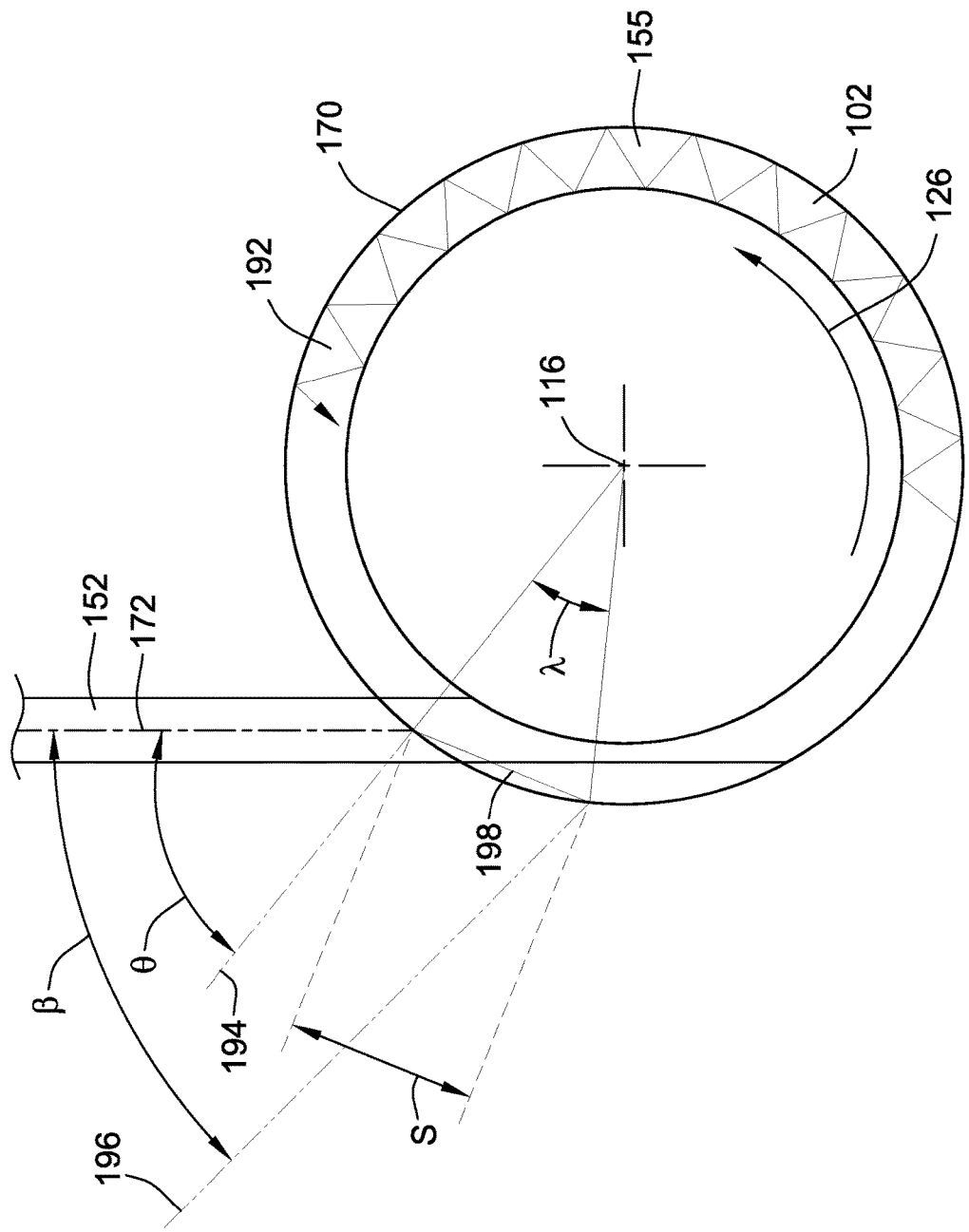
FIG. 5 is a simplified schematic illustration of top view of a glass container being inspected by the first inspection arrangement of FIG. 3.

With reference to FIG. 5, a simplified top view of the first laser beam 152 is illustrated intersecting with the outer periphery 170 of the glass container 102. The optical inspection system 134 is configured to direct the first laser beam 152 such that it forms an angle of incidence θ relative to a plane normal (illustrated by dashed line 194) such that total internal reflection of at least one of the wavelengths of light of the first laser beam 152 occurs.

The angle of incidence θ is such that the first laser focus axis 172 and the first laser beam 152 are incident to the glass container almost parallel to the edge of the glass container at a slight grazing angle. This angle of incidence θ allows the light of the laser beam 152 to enter into the sidewall 155 of the glass container 102. The light that enters into the sidewall 155 is then confined within the middle layer of the glass by total internal reflection.

For this to occur angle of incidence θ must be greater than a critical angle θ, Pursuant to Snell's Law:

$$\theta_c = \arcsin(n2/n1) \qquad \text{Equation (1)}$$

wherein n2 is the index of refraction of the material surrounding the material in which the light wave is propagating and n1 is the index of refraction of the material in which the light wave is propagating.

Flint glass, for example, has an index of refraction of approximately 1.61 with a range of between 1.52 and 1.92 for impure flint glass. As such, $\theta_c$ for impure flint glass will be between arcsin (1/1.52) and arcsin (1/1.92) or between 31.3°-41°. As such, angle of incidence θ must be greater than approximately 60° degrees such that total internal reflection will occur for impure flint glass. In the illustrated embodiment, angle of incidence θ of the first laser beam is greater than 65° but less than 90°.

The camera 154 is oriented and configured to capture light that is reflected out of the sidewall 155 of the glass container 102, particularly due to the presence of a check defect. In one embodiment, the camera 154 is a high speed line scan camera. However, other embodiments can incorporate an area array camera. If light of the first laser beam 152 is trapped within the sidewall 155 of the glass container, the camera 154 will not see anything such that the feedback signal of the camera 154 would represent a black image. However, if a defect exists in the sidewall 155 of the container such as, for example a crack or a check, the trapped light within the sidewall 155 will be reflected and caused to exit out of the sidewall 155. This reflected light can be captured by the camera 154. The captured images and output of the camera 154 can be processed using existing processing techniques and algorithms to determine if a defect is actually present in the glass container 102 and more particularly if a defect sufficient to cause the glass container 102 to be rejected exists. If such a defect is determined, the glass container 102 will be removed from the stream of bottles by downstream components such as by using a puff of compressed air or other known fashion.

The analysis of the data sensed by camera 154 may be processed by controller 148 or sent to a separate processing system for analysis.

Internally reflected light is shown schematically in FIG. 5 as the arrow that is trapped within the inner and outer surfaces of the sidewall of the glass container. If an imperfection, e.g. check defect, is present in the sidewall, the light will contact the check defect and will exit the glass container, typically as a bright flash.

With continued reference to FIG. 5, the camera 154 is positioned and oriented relative to the inspection location and the first laser source 150 such that a camera focus axis 196 forms camera-to-first laser angle β of between about 15 and 41 degrees and more preferably between 17 and 32 degrees and more preferably of between 24 and 28 degrees when viewed down the container axis of rotation 116.

Preferably, the camera focus axis 196 intersects the outer periphery 170 of the glass container 102 at a different location than where the laser beam 152 and particularly the corresponding first laser focus axis 172 intersect the outer periphery 170 when viewing along the container rotational axis 116. This reduces the amount of light noise that will be observed by camera 154. Preferably, the intersection points are offset by an angle λ about the outer periphery 170 when measured relative to the container axis of rotation 116 of between about 25 and 45 degrees and more preferably between about 30 and 40 degrees. In other embodiments, the intersection points may have a spacing defined by a chord 198 between the intersection points having a length S that is sufficient to prevent reflected light from laser beam 152 that does not get trapped within the glass container from providing false positive identification of a defect, e.g. to avoid unnecessary light noise being exposed to the camera.

Because the glass container 102 is rotated at least 360° about the container axis of rotation 116 by rotator 120, any defect should pass in front of the camera 154 for detection. However, to improve the accuracy of the glass container inspection device to avoid allowing defective bottles to pass through the system undetected, it is desirable to rotate the glass container 102 at least 720° and more preferably at least 900°. When 900° of rotation is used, any defect should pass by the camera 154 at least twice. The large degree of rotation should compensate for any potential slippage between rotator 120 and the glass container 102.

Figure 6:
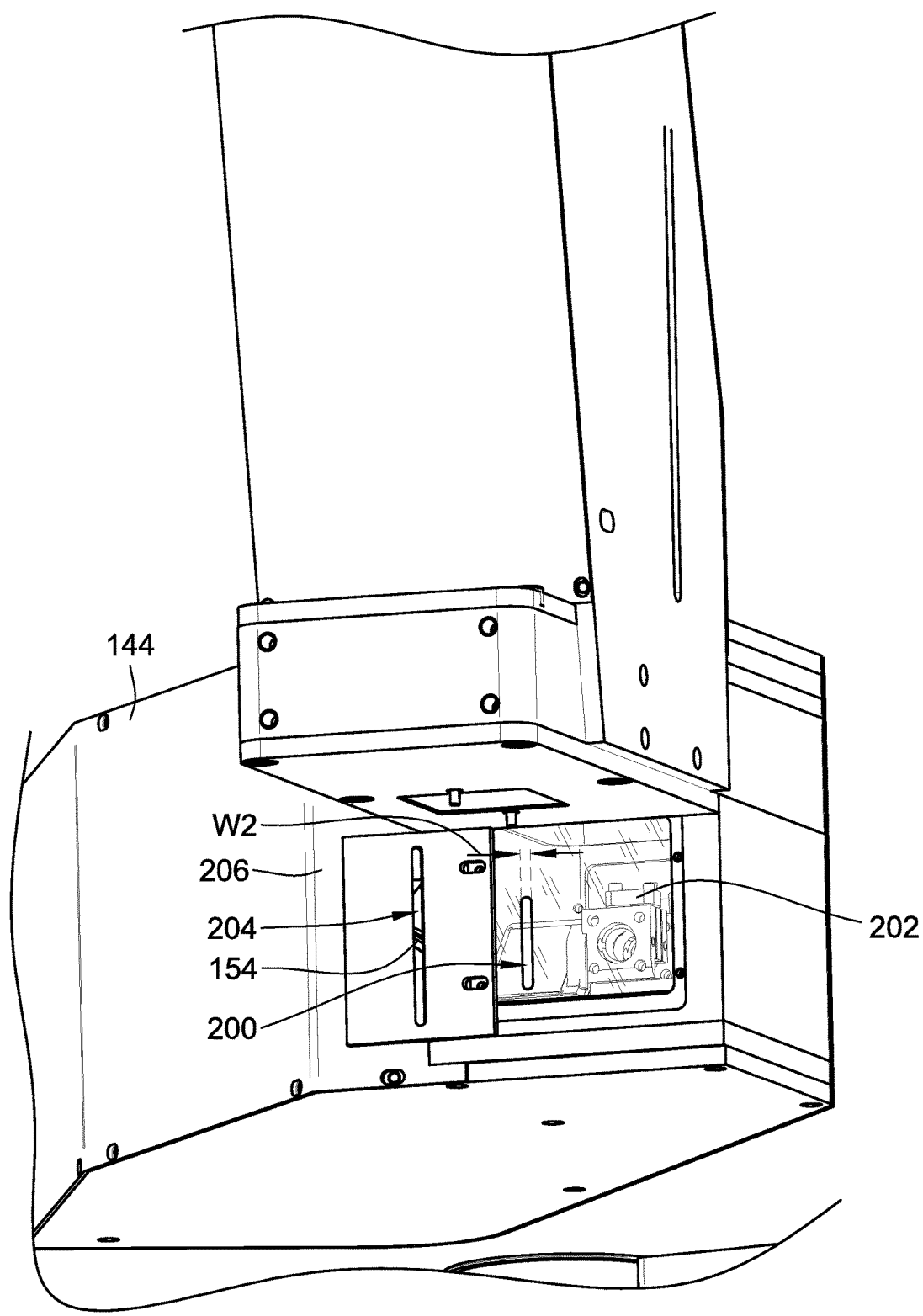
FIG. 6 is a further partial illustration of the first inspection arrangement.

With reference to FIG. 6, the first housing 144 houses the camera 154 and the first laser source 150, ideally in separate compartments. The housing 144 defines a first aperture 200 through which the first laser beam 152 is transmitted as it exits the first housing 144. The first aperture 200 has a width W2 of approximately between 4 and 6 millimeters and more preferably approximately 5 millimeters. The aperture 200 is formed in a front panel 202 and the first laser beam 152 has an angle of incidence with the front panel of approximately 0°, e.g, it is preferably perpendicular to the front panel 202.

First housing 144 defines a second aperture 204 through which the camera 154 views the glass container 102 within the inspection location. Preferably, the angle of incidence between the camera 154 and the panel 206 through which second aperture 204 is formed is 0°. As such, panel 206 and panel 202 are angled relative to one another at a same angle as the camera-to-first laser angle β (e.g. between about 15 and 41 degrees and more preferably between about 17 and 32 degrees and more preferably of between 24 and 28 degrees) when viewed down the container axis of rotation 116.

Figure 7:
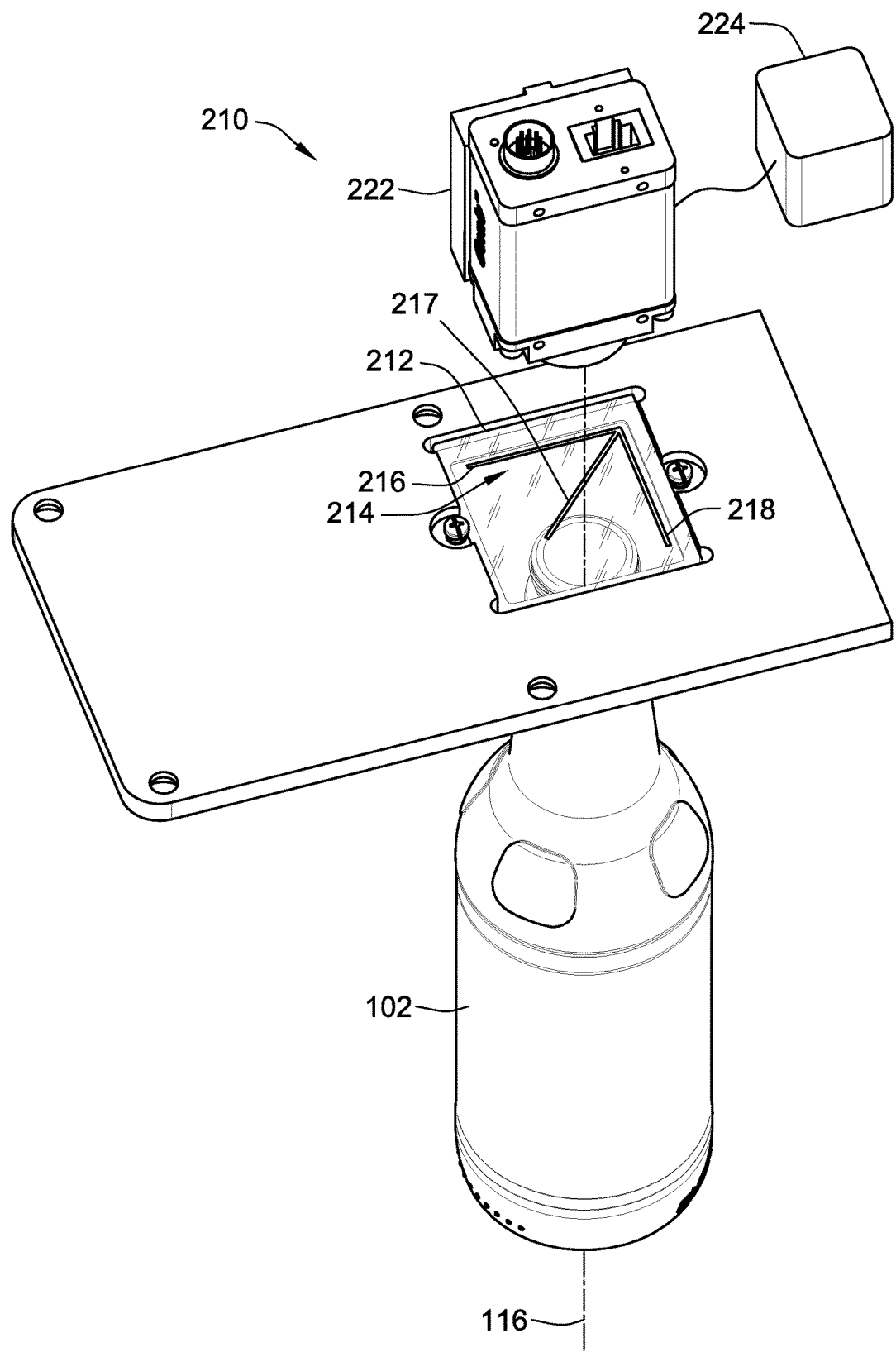
FIG. 7 is a partial illustration of an alignment guide for aligning the optical inspection system of the glass container inspection device of FIG. 1.

As noted above, the position of the optical inspection system 134 can be changed to accommodate glass containers 102 of different sizes and shapes. FIG. 7 illustrates, in simplified form, an alignment guide 210 used to align the optical inspection system 134 relative to a given glass container 102 located within the inspection location.

The alignment guide 210 includes a viewing window 212 that defines a reticle 214 that includes alignment lines 216, 218 that extend relative to one another at a right angle within a plane normal to the container rotational axis 116. A third alignment line 217 bisects the first and second alignment lines 216, 218. The viewing window 212 and corresponding reticle 214 are fixedly attached to the camera 154 and first laser source 150 such that adjustment of the position of the camera 154 and first laser source within a plane normal to the container axis of rotation 116 causes a corresponding change in position of the viewing window 212 and corresponding reticle 214.

Figure 8:
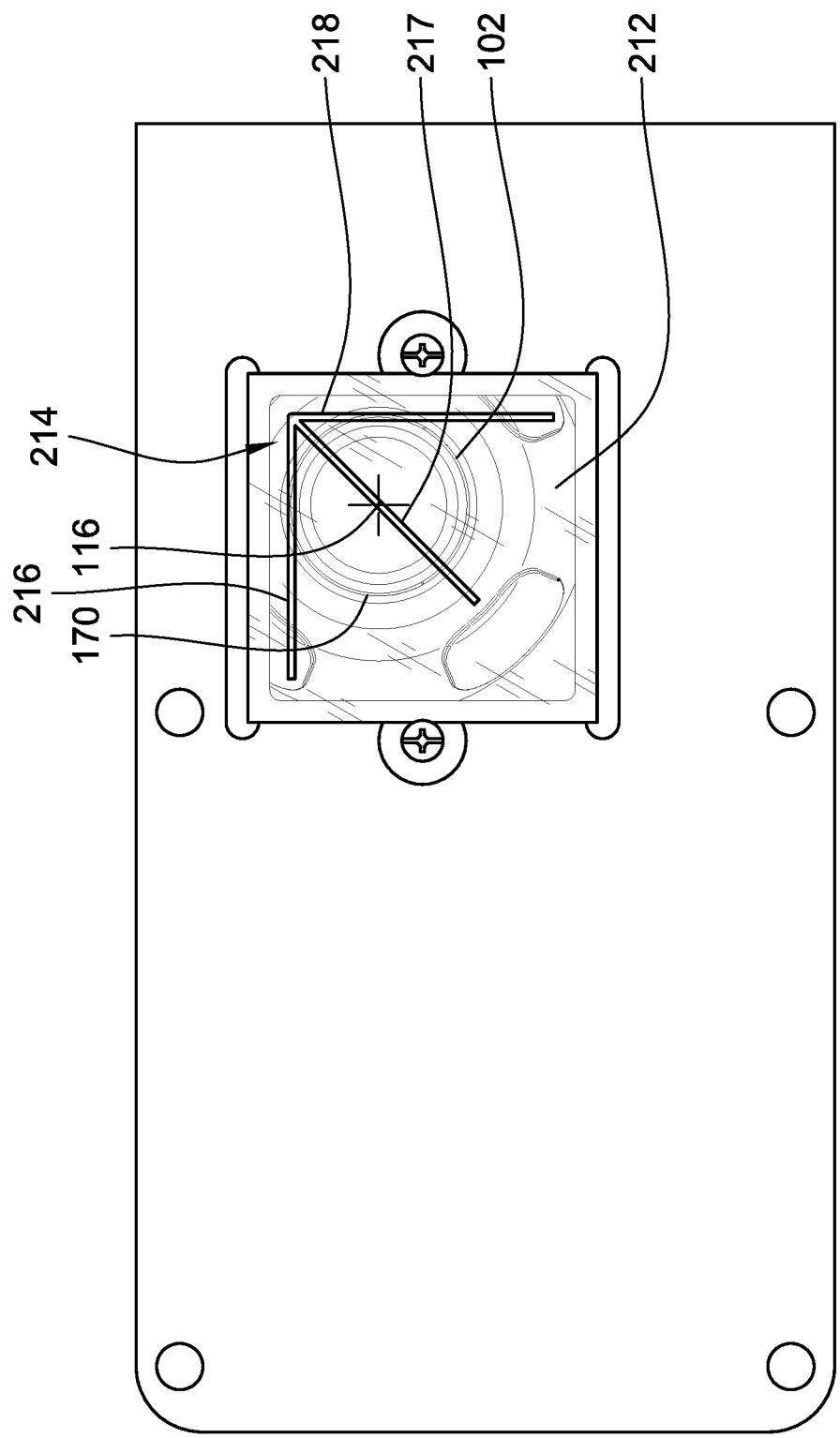
FIG. 8 is a further partial illustration of the alignment guide of FIG. 7 illustrating a glass container within an inspection location of the system positioned within a reticle of the alignment guide.

With additional reference to FIG. 8, to properly align the camera 154 and first laser source 150, a user, looking parallel to the container axis of rotation 116 aligns the first and second alignment lines 216, 218 such that they are both substantially tangent to the outer periphery 170 of the desired portion of the glass container to be inspected. These adjustments can be performed manually or automatically. Further, third alignment line 217 preferably aligns with axis of rotation 116.

With reference to FIG. 7, in one embodiment, the alignment guide 210 includes an alignment camera 222 aligned vertically above the viewing window 212 such that the reticle 214 can be viewed relative to the glass container 102 positioned within the inspection location. The alignment camera 222 is positioned to view the glass container 102 and the alignment lines 216, 217, 218 at least when both of alignment lines 216, 218 are substantially tangent to the outer periphery 170 of the glass container 102.

The alignment camera 222 is operably coupled to a display 224 that the operator can view while adjusting the position of the optical inspection system. The alignment camera 222 is housed within the second housing 146 (see FIG. 1).

While the first laser source 150 is primarily targeted at identifying vertically oriented defects, such as defects that have a component that extends generally parallel to the container axis of rotation 116, the optical inspection system 134 may also include a second laser source 240 (FIGS. 9-10) that is housed within the second housing 146 (see FIG. 1).

Figure 9:
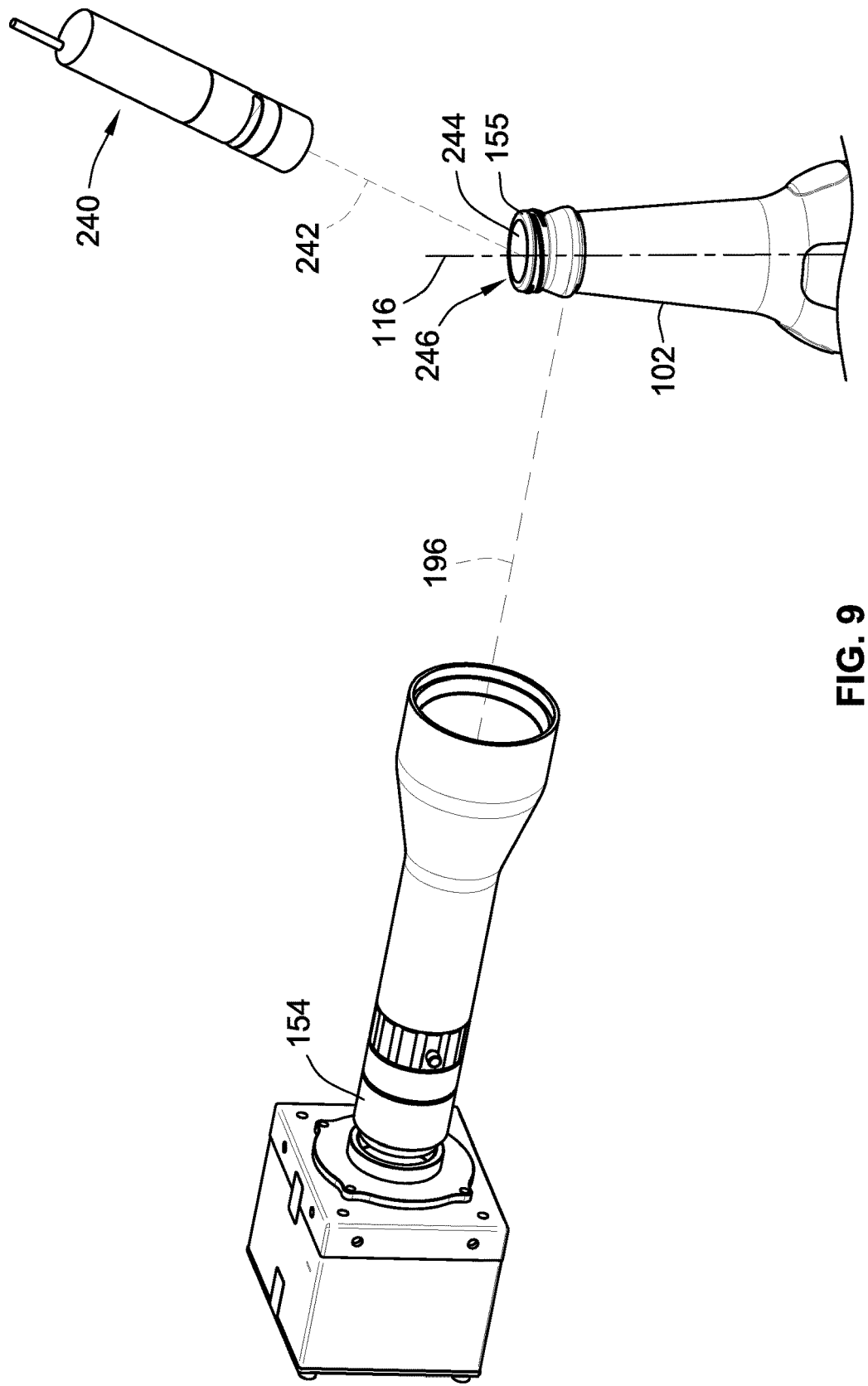
FIG. 9 is a simplified illustration of a second inspection arrangement of the glass container inspection device of FIG. 2.
Figure 10:
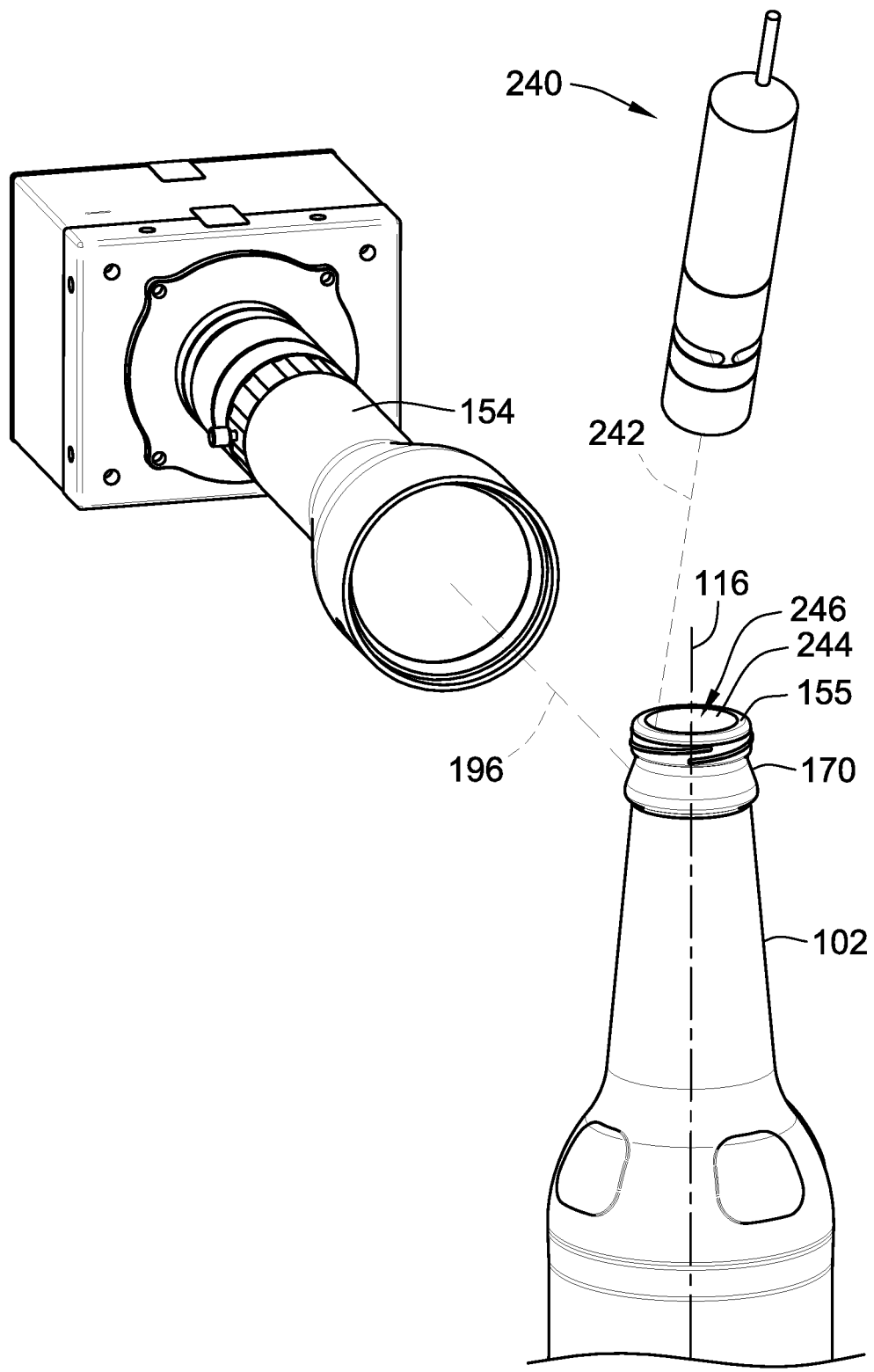
FIG. 10 is a further simplified illustration of the second inspection arrangement of FIG. 9.

The second laser source 240 defines and directs a second laser beam 242 from a location vertically above (where vertical is defined by the container axis of rotation 116) and through the viewing window 212 that includes reticle 214 (see e.g. FIGS. 7-8, not shown in FIGS. 9-10 for clarity purposes). The second laser beam 242 is directed towards an inner surface 244 of the sidewall 155 of the glass container 102 in a vertically downward direction through the opening 246 of the finish of the glass container 102. The second laser beam 242 is directed at an angle of about between about 10 and 45° and more particularly between about 20 and 30° relative to the inner surface 244 of the sidewall 155 of the glass container 102. Again, the angle is selected to promote total internal reflection of the second laser beam 242. As the second laser beam 242 is directed more vertically downward, the second laser beam 242 has a much smaller cross section and may be in the form of a concentrated dot having dimensions of between 50 and 5000 micrometers. However, other dimensions may be used depending on the shape and configuration of the glass container being inspected. The second laser focus axis in the illustrated embodiment will be the same as the line representing the second laser beam 242 due to the dimensions of the second laser beam 242 and is thus not separately called out in the figures.

Ideally, the light of the second laser beam 242 is totally internally reflected within the sidewall 155 of the glass container 102 and only exits the glass container, at least proximate the finish, due to defects in the sidewall 155 of the glass container 102. More particularly, due to the more vertical orientation of the second laser beam 242, the second laser source 240 is intended on identifying horizontally oriented defects that may not be contacted or otherwise reflected by the light generated by the first laser beam 152 of the first laser source 150.

The second laser beam 242 is directed towards the inner surface 244 at a position proximate the intersection point of the camera focus axis such that any light that is reflected out of the sidewall 155 is captured or sensed by camera 154. In the illustrated embodiment, the second laser beam 242 is configured such that the second laser beam 242 generates light having a wavelength of light that is between 620-750 nm more preferably between 640-700 nm and even more preferably 660 nm (red).

While the first laser source 150 includes three wavelength laser sources 156, 158, 160, an embodiment could include only a single wavelength laser source. However, the application of the system would be more limited and particularly to a more limited range of colors of glass that could be satisfactorily inspected. Similarly, while the second laser source 240 only includes a single laser source for producing a single wavelength of light, other embodiments could include more laser sources for producing more wavelengths of light similar to the first laser source 150 described above. Such a configuration of more wavelengths of light could use a laser beam delivery optics similar to the first laser beam delivery optics 174 described above for operably aligning the plurality of laser beams into a single laser beam that is incident to the surface of the glass container 102.

Figure 11:
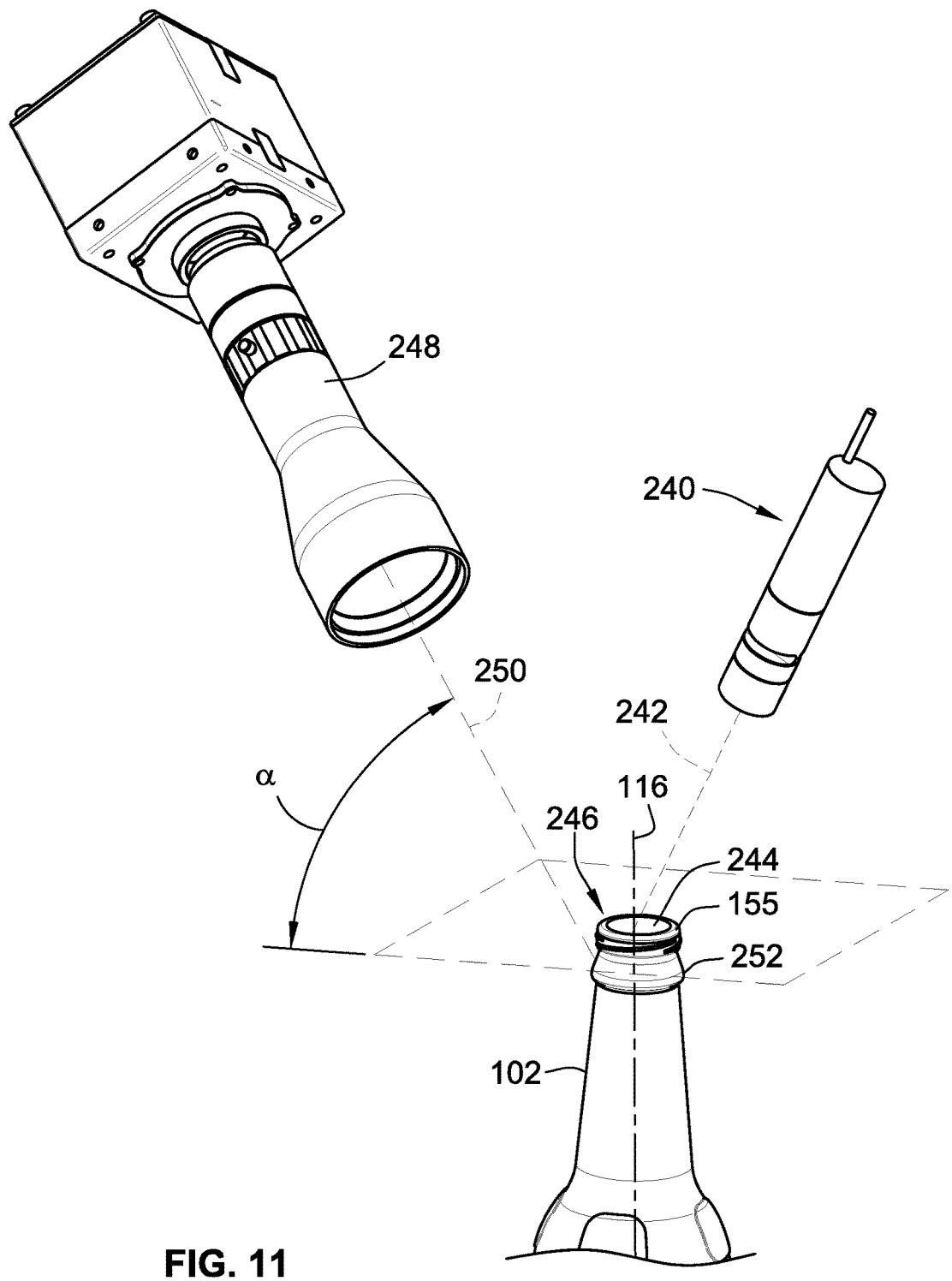
FIG. 11 is an alternative embodiment of a second inspection arrangement that utilizes a separate camera for sensing horizontal defects
Figure 12:
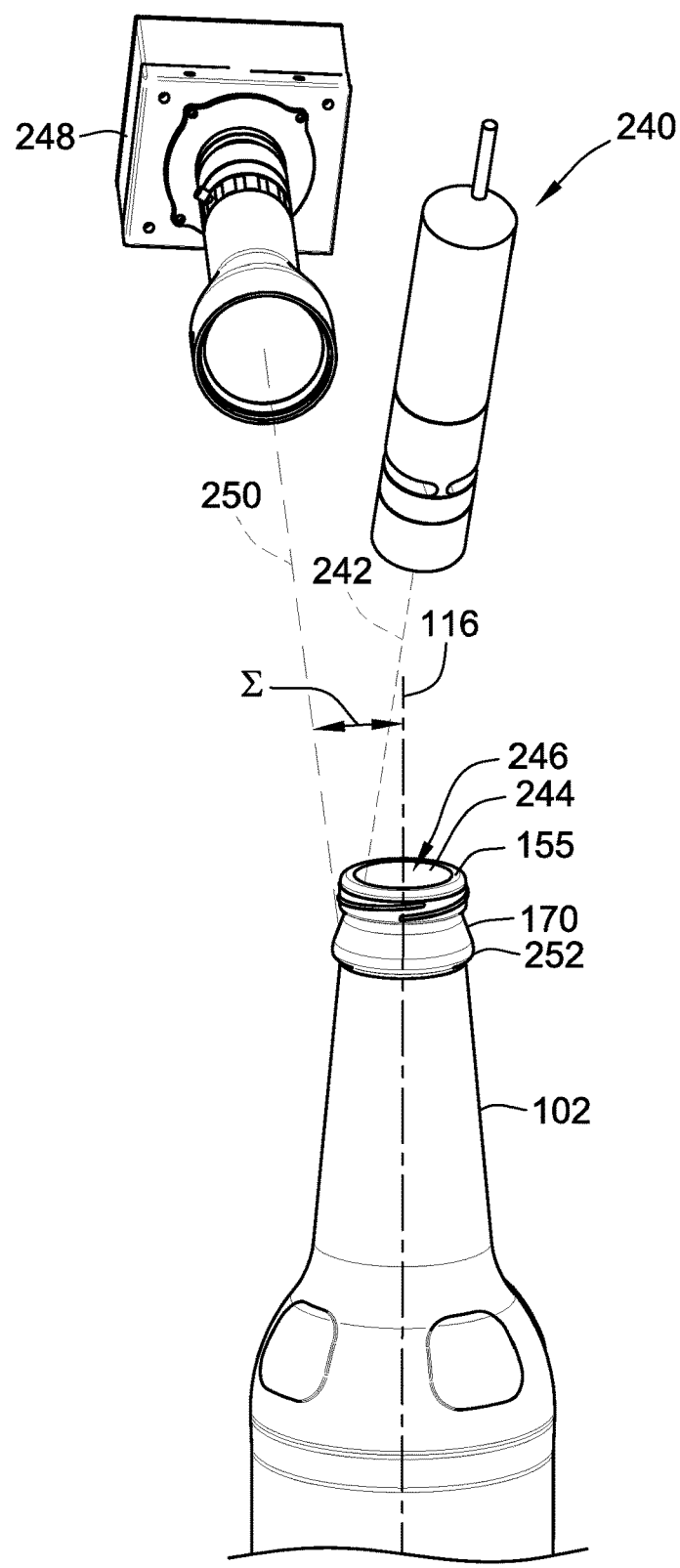
FIG. 12 is a further simplified illustration of the second inspection arrangement of FIG. 11

While the embodiment of FIGS. 9 and 10 use camera 154 to sense or capture light that is reflected out of the sidewall 155, FIGS. 11 and 12 illustrate a further embodiment that utilizes a separate camera 248 to sense or capture light that is reflected out of the sidewall 155. This camera 248 is located vertically above the glass container 102 much like the second laser source 240 to better capture light that is reflected from horizontal defects out of sidewall 155. Preferably, the second camera defines a camera focus axis 250 that is aimed generally at the finish and more particularly proximate the bead 252 of the glass container 102. However, the camera can be aimed to view portions of the bottle above and below the bead 252 including parts of the threads of the finish.

As illustrated in FIG. 11, preferably, the camera 248 is aimed such that camera focus axis 250 forms an angle α of between about 25 and 45° and more preferably between about 35 and 40° relative to horizontal. Horizontal would generally be viewed by a plane orthogonal to the container axis of rotation 116.

As illustrated in FIG. 12, camera focus axis 250 is offset from container axis of rotation 116 and forms an angle ε of between about 15 and 25° and more preferably about 20° therebetween.

Further, lasers having different wavelengths of light could be used for detecting defects in different color glass. For instance, it is contemplated that wavelengths of light in the range of 760-900 nm range and more particularly a range of approximately 810-850 nm and more particularly 830 nm could be used as well as wavelengths of light in the 375-425 nm range and more particularly 390-410 nm range and even more particularly 405 nm could be used for other colors of glass. For instance, by using wavelengths outside of the visible spectrum, it is contemplated that glass containers formed from black colored glass could be inspected for check defects.

Further, it is contemplated that some embodiments will include at least 5 different laser sources that are operably aligned to form a single laser beam namely the five different wavelength ranges described above. In one embodiment, each laser beam could be provided with at least 6 laser sources producing different wavelengths of light. For instance, there could be multiple laser sources for each of the infrared, ultraviolet and visible light spectrums.

Additionally, the embodiments above illustrate the use of an optical inspection system 134 that forms a laser beam 152 from laser source 150 focused at the glass container 102 in a single orientation (see e.g. FIG. 5) used to identify vertically oriented defects or at least defects that have a vertically oriented component.

Figure 13:
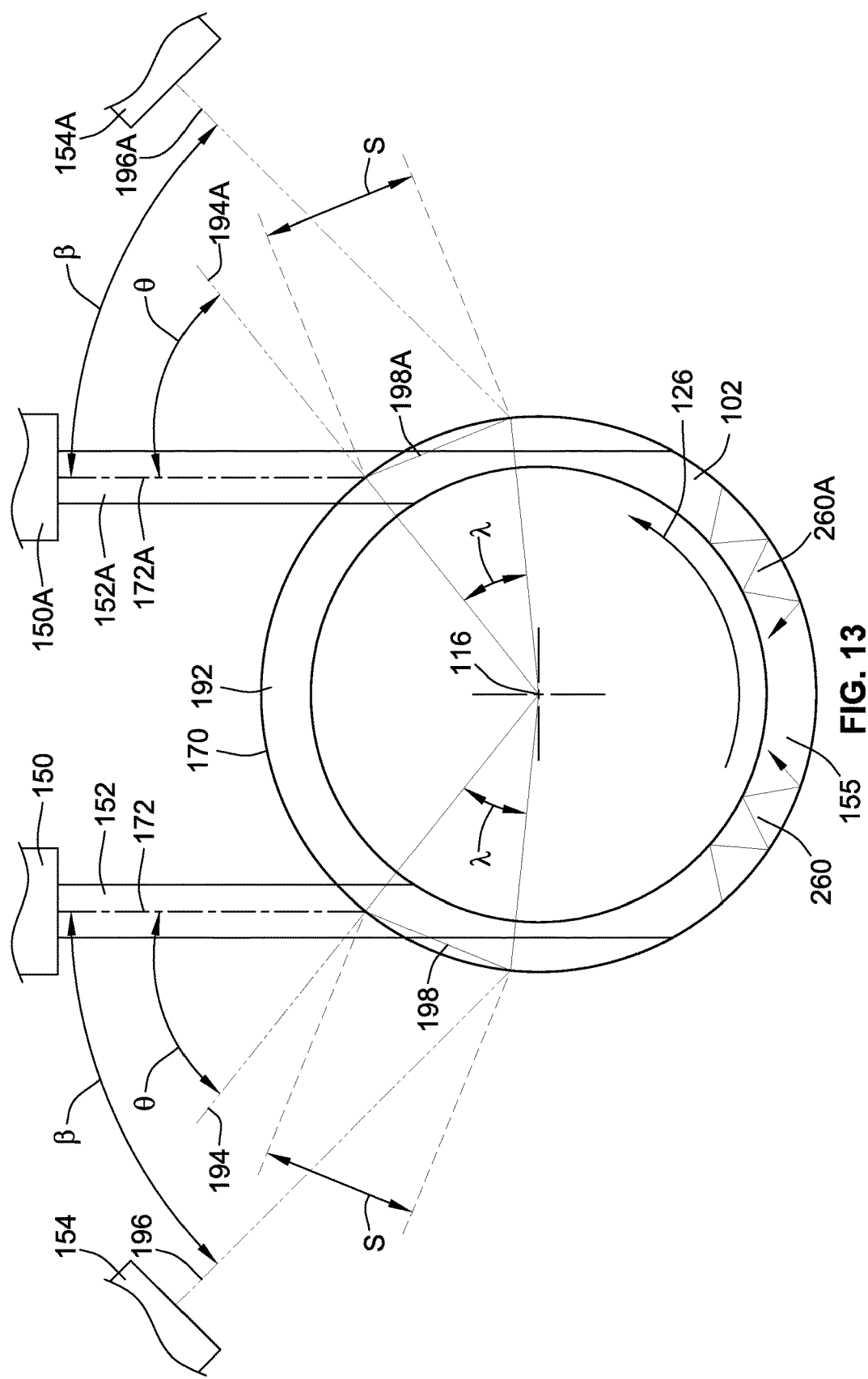
FIG. 13 is a schematic representation of a first inspection arrangement similar to that of FIG. 5 but illustrating the use of multiple laser sources and cameras for sensing left and right handed vertical defects

With reference to FIG. 13, a portion of an alternative embodiment of an optical inspection system is illustrated schematically only that includes two laser sources 150, 150A for inspecting for vertically oriented defects. Laser source 150 is similar to and includes all of the features and components as described previously. Laser source 150A is similar to laser source 150 and includes all of the features and components thereof but is oriented in an opposite direction. Internally reflected light of laser beam 152 is represented by zig-zag line 260 and is directed in a first direction around axis of rotation 116. Internally reflected light of laser beam 152A directed from laser source 150A along focus axis 172A is represented by zig-zag line 260A and is directed in a second opposite direction around axis of rotation 116. Camera 154A and laser source 150A have similar angle orientations relative to container 102 but on opposite sides of the container 102 such that the light generated thereby moves in the opposite direction.

Figure 14:
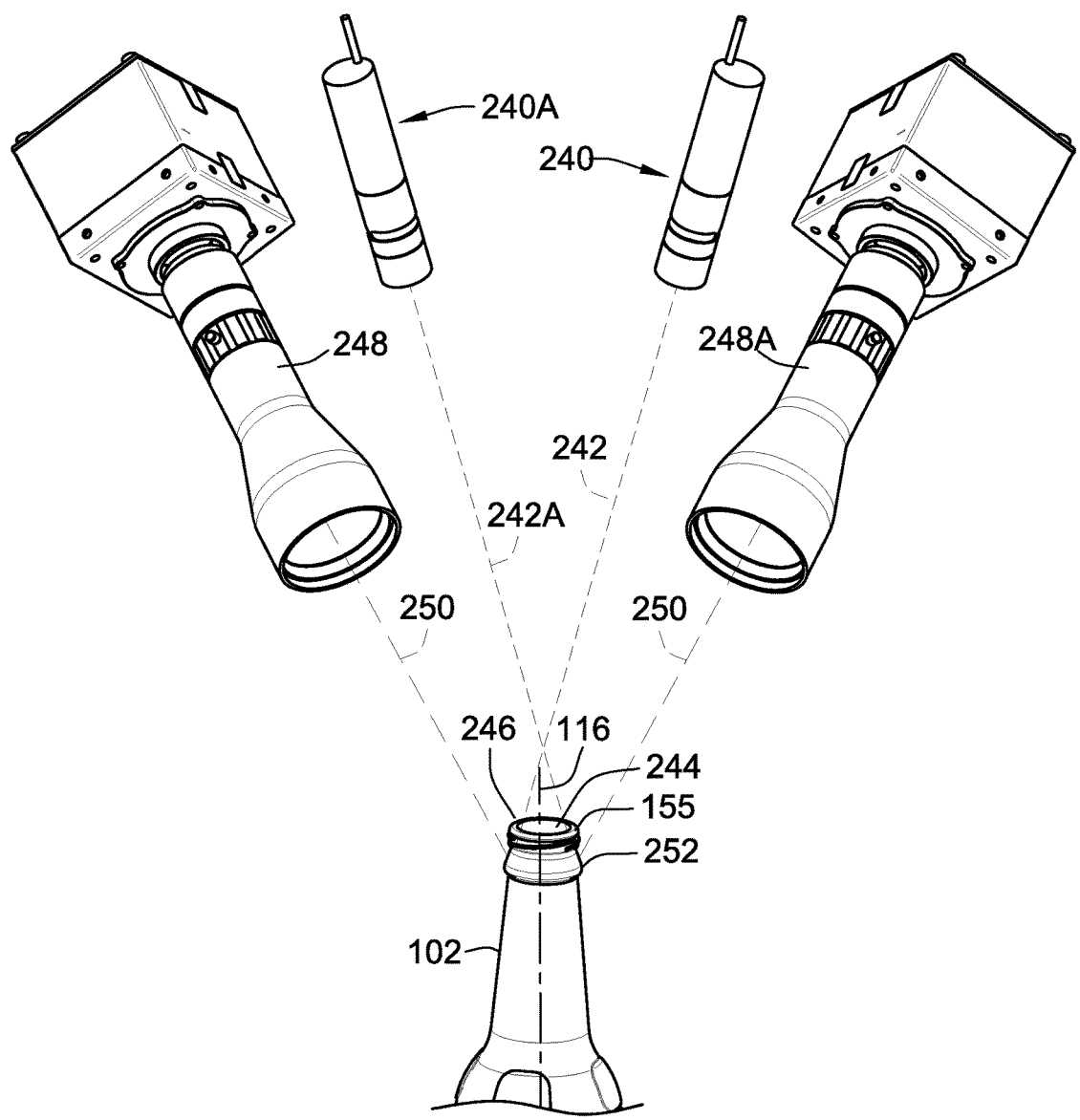
FIG. 14 is a simplified illustration of an alternative embodiment of a second inspection arrangement for sensing horizontal defects that uses multiple laser sources and cameras for sensing horizontal defects.
Figure 15:
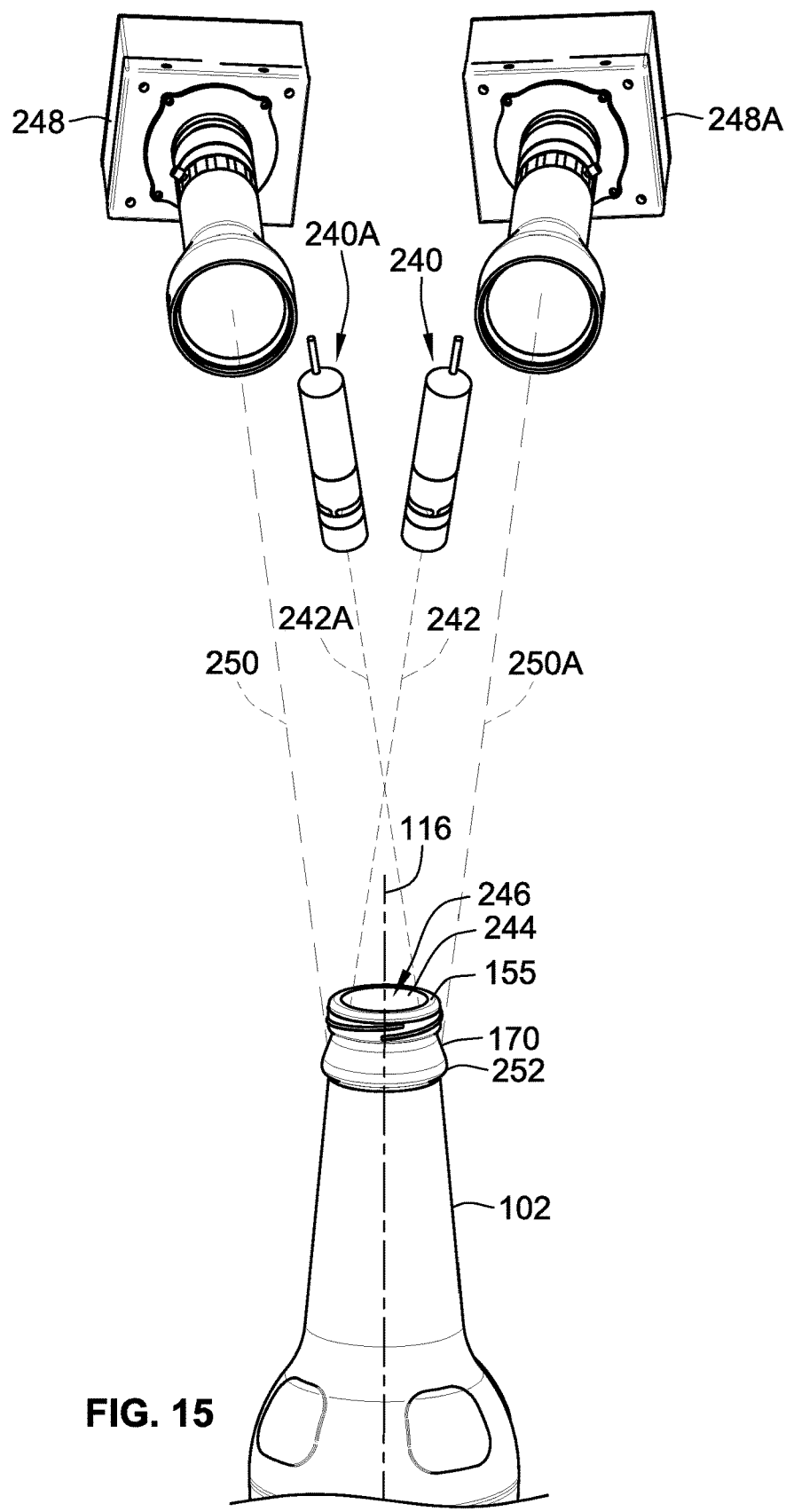
FIG. 15 is a second illustration of the embodiment of FIG. 14.

The use of two separate laser sources 150, 150A and cameras 154, 154A better tests for vertical defects if the vertical defects have left or right handed tendencies. For instance, some vertical defects will tend to reflect light out of the container 102 in a first direction while other vertical defects will tend to reflect light out of the container 102 in an opposite direction. By having laser sources 150, 150A oriented opposite one another both of these defects will be more likely to be detected. However, it is not necessary for embodiments to have two laser sources 150, 150A, FIGS. 14 and 15 illustrate a portion of a further embodiment of an optical inspection system that incorporates a pair of laser sources 240, 240A and a pair of cameras 248, 248A for inspecting for horizontal defects. The pair of laser sources 240, 240A are oriented opposite one another but at similar angles relative to the container 102. Laser beams 242, 242A are again directed through the opening 246 in the finish of the container to contact the inner surface of the container 102. The cameras 248, 248A have their respective camera focus axis 250, 250A again directed proximate the bead 252 of the container 102.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A glass container inspection device for inspecting a finish region of the glass container comprising:
    a rotator configured to rotate a selected glass container located in an inspection location at least 360 degrees;
    a first laser source configured to produce a first collimated laser beam, the first laser source being configured to direct the first collimated laser beam towards the inspection location, the first collimated laser beam forming an angle of incidence with the selected glass container being greater than or equal to a critical angle for producing internal reflection of the first collimated laser beam within the selected glass container; and
    a camera directed at the inspection location for detecting light that escapes from the selected glass container as a result of the internally reflected first collimated laser beam intersecting a defect in the selected glass container;
    an alignment mechanism for simultaneously adjusting a position of the first laser source and the camera parallel to a plane normal to a container axis of rotation about which the selected glass container is rotated by the rotator;
    an alignment guide being carried with the camera and the first laser source when the alignment mechanism adjusts the position of the first laser source and the camera, the alignment guide defining a pair of alignment lines extending at a right angle to one another in the plane normal, wherein both alignment lines are positioned tangent to an outer periphery of a selected glass container within the inspection location when viewed along the container axis of rotation to set a position of the alignment mechanism.

2. The glass container inspection device of claim 1, wherein the first laser source is a multi-wavelength laser source configured such that the first collimated laser beam is a multi-wavelength collimated laser beam, the multi-wavelength laser source including:
    a first wavelength laser source configured to produce a first wavelength collimated laser beam of a first wavelength of light;
    a second wavelength laser source configured to produce a second wavelength collimated laser beam of a second wavelength of light different than the first wavelength of light; and
    a third wavelength laser source configured to produce a third wavelength collimated laser beam of a third wavelength of light different than the first and second wavelengths of light;
    the multi-wavelength light source configured to direct the multi-wavelength collimated laser beam towards the inspection location, the multi-wavelength collimated laser beam forming an angle of incidence with the selected glass container that is greater than or equal to a critical angle for producing total internal reflection of at least one of the first, second and third wavelength collimated laser beams of the multi-wavelength collimated laser beam within the selected glass container.

3. The glass container inspection device of claim 1, wherein the first wavelength of light is between 440-490 nm, the second wavelength of light is between 495-570 nm and the third wavelength of light is between 620-750 nm.

4. The glass container inspection device of claim 3, wherein the first wavelength of light is between 440-460 nm, the second wavelength of light is between 510-530 nm and the third wavelength of light is between 630-650 nm.

5. The glass container inspection device of claim 4, wherein the first laser source has an excitation source having a power value of between 5-150 milliwatts average power continuous wave.

6. The glass container inspection device of claim 5, wherein the first laser source is operably located and oriented relative to the inspection location such that the first collimated laser beam has a first dimension parallel to a first axis of between 20 and 60 millimeters and a second dimension along a second axis perpendicular to the first dimension and first axis of between 25 and 100 micrometers.

7. The glass container inspection device of claim 6, wherein the rotator rotates the selected glass container about a container axis of rotation, the first axis of the first collimated laser beam being at an angle of between 0 and 15 degrees relative to the container axis of rotation in a plane orthogonal to a focus axis of the first collimated laser beam.

8. The glass container inspection device of claim 1, further comprising a glass container transport arrangement for transporting the selected glass container into the inspection location, configured for stopping the selected glass container within the inspection location for a predetermined period of time at which time the rotator rotates the selected glass container at least 360 degrees, and configured for transporting the selected bottle out of the inspection location.

9. The glass container inspection device of claim 1, wherein the first laser source is configured to direct the first collimated laser beam towards the selected glass container at an angle of incidence of at least 65 degrees and less than 90 degrees.

10. The glass container inspection device of claim 1, wherein the camera defines a camera focus axis directed toward the inspection location, the camera focus axis extending angularly relative to a first laser focus axis of the first laser source along which the first collimated laser beam travels at a camera-to-laser angle of between 17 and 32 degrees.

11. The glass container inspection device of claim 10, wherein the first laser source and the camera are spaced from the inspection location such that the camera focus axis and the first laser focus axis intersect an outer periphery of a glass container within the inspection location prior to intersecting when the camera focus axis and the first laser focus axis are viewed in a direction extending parallel to a container axis of rotation about which the selected glass container is rotated by the rotator.

12. The glass container inspection device of claim 1, further including:
 an alignment camera, the alignment camera positioned to view a selected glass container within the inspection location and the alignment lines, at least when, the alignment lines are both tangent to the outer periphery of the selected glass container; and
 an alignment display operably connected to alignment camera displaying an output of the alignment camera.

13. The glass container inspection device of claim 2, further including first collimated laser beam delivery optics including:
 a second laser source redirection structure optically interposed between the second laser source and the inspection location for redirecting the second wavelength collimated laser beam produced by the second wavelength laser source along a first laser focus axis;
 a third wavelength laser source redirection structure optically interposed between the third wavelength laser source and the inspection location for redirecting the third wavelength collimated laser beam produced by the third wavelength laser source along the first laser focus axis such that the first, second and third wavelength collimated laser beams are coincident when they intersect an outer periphery of a selected glass container within the inspection location.

14. The glass container inspection device of claim 13, wherein the second wavelength laser source redirection structure is made of a material that allows the first wavelength of light to pass therethrough and the second wavelength of light is reflected and the third laser source redirection structure is made of a material that allows the first and second wavelengths of light to pass therethrough and the third wavelength of light is reflected.

15. The glass container inspection device of claim 14, further including a first laser source redirection structure optically interposed between the first laser source and the inspection location for redirecting the first wavelength collimated laser beam produced by the first wavelength laser source along the first laser focus axis.

16. The glass container inspection device of claim 1, wherein the first collimated laser beam of the first laser source travels along a first laser focus axis as the first collimated laser beam contacts an outer periphery of the selected glass container;
 further including a fifth laser source configured to produce a fifth collimated laser beam traveling along a fifth laser focus axis different than the first laser focus axis, the fifth laser source being configured to direct the fifth collimated laser beam towards the selected glass container in the inspection location at a fifth angle of incidence with the selected glass container being greater than or equal to a critical angle for producing internal reflection of the fifth collimated laser beam within the selected glass container, the fifth laser focus axis being at a skew angle relative to a plane normal to a container axis of rotation about which the rotator rotates the selected glass container.

17. The glass container inspection device of claim 16, wherein the second laser focus axis is directed to intersect an inside of an opening of the selected glass container such that horizontal defects can be detected using a second camera.

18. The glass container inspection device of claim 1, wherein the rotator is configured to rotate the selected glass container at least 720 degrees while in the inspection location.

19. The glass container inspection device of claim 1, further comprising a fourth laser source configured to produce a fourth collimated laser beam, the fourth laser source being configured to direct the fourth collimated laser beam towards the inspection location to form an angle of incidence with the selected glass container being greater than or equal to a critical angle for producing internal reflection of the fourth collimated laser beam within the selected glass container; and
 a second camera directed at the inspection location for detecting light that escapes from the selected glass container as a result of the internally reflected fourth collimated laser beam intersecting a defect in the selected glass container;
 the first and fourth laser sources being oriented such that the first and fourth collimated laser beams travel in opposite directions within the selected glass container.

20. A method of inspecting the finish region of the glass container comprising:
 rotating a selected glass container located in an inspection location at least 360 degrees;
 producing a first collimated laser beam with a first laser source;
 directing the first collimated laser beam towards the inspection location, the first collimated laser beam forming an angle of incidence with the selected glass container being greater than or equal to a critical angle for producing internal reflection of the first collimated laser beam within the selected glass container;
 detecting light that escapes from the selected glass container as a result of the internally reflected first collimated laser beam intersecting a defect in the selected glass container;
 adjusting, simultaneously, a position of the first laser source and a camera for detecting light that escapes parallel to a plane normal to a container axis of rotation about which the selected glass container is rotated;

wherein adjusting the position of the first laser source and the camera includes using an alignment guide being carried with the camera and the first laser source when the position of the first laser source and the camera is adjusted, the alignment guide defining a pair of alignment lines extending at a right angle to one another in the plane normal; and wherein adjusting the position of the first laser source and the camera includes aligning both alignment lines tangent to an outer periphery of a selected glass container within the inspection location when viewed along the container axis of rotation to set a position of the alignment mechanism.

21. The method of claim 20, wherein producing the first collimated laser beam includes producing a multi-wavelength collimated laser beam and the first laser source is a multi-wavelength laser source including a first, second and third wavelength laser source, producing the multi-wavelength collimated laser beam includes:

producing a first wavelength collimated laser beam of a first wavelength of light with the first wavelength laser source;

producing a second wavelength collimated laser beam of a second wavelength of light different than the first wavelength of light with the second wavelength laser source; and producing a third wavelength collimated laser beam of a third wavelength of light different than the first and second wavelengths of light with the third wavelength laser source;

wherein directing the first collimated laser beam includes directing the multi-wavelength collimated laser beam towards the inspection location, the multi-wavelength collimated laser beam forming an angle of incidence with the selected glass container that is greater than or equal to a critical angle for producing total internal reflection of at least one of the first, second and third wavelength collimated laser beams of the multi-wavelength collimated laser beam within the selected glass container.

22. The method of claim 21, wherein the first wavelength of light is between 440-490 nm, the second wavelength of light is between 495-570 nm and the third wavelength of light is between 620-750 nm.

23. The method of claim 21, wherein the first wavelength of light is between 440-460 nm, the second wavelength of light is between 510-530 nm and the third wavelength of light is between 625-665 nm.

24. The method of claim 20, wherein the first laser source has an excitation source having a power value of between 5-150 milliwatts average power continuous wave.

25. The method of claim 20, wherein the first collimated laser beam has a first dimension parallel to a first axis of between 20 and 60 millimeters and a second dimension along a second axis perpendicular to the first dimension and first axis of between 25 and 100 micrometers.

26. The method of claim 25, wherein rotating the selected glass container includes rotating the selected glass container about a container axis of rotation, the first axis of the first collimated laser beam being at an angle of between 0 and 15 degrees relative to the container axis of rotation in a plane orthogonal to a focus axis of the first collimated laser beam.

27. The method of claim 20, further comprising:

transporting the selected glass container into the inspection location;

stopping the selected glass container within the inspection location for a predetermined period of time during which the step of rotating the selected glass container occurs while the selected glass container is stopped within the inspection location; and transporting the selected bottle out of the inspection location.

28. The method of claim 20, wherein rotating includes rotating the selected glass container at least 720 degrees while in the inspection location.

29. The method of claim 20, wherein directing the first collimated laser beam includes directing the first collimated laser beam towards the selected glass container at an angle of incidence of at least 65 degrees and less than 90 degrees.

30. The method of claim 20, wherein detecting light that escapes from the selected glass container is performed using a line scan camera defining a camera focus axis directed toward the inspection location, the camera focus axis extending angularly relative to a first laser focus axis of the first laser source along which the first collimated laser beam travels at a camera-to-laser angle of between 17 and 32 degrees.

31. The method of claim 30, wherein the first laser source and the camera are spaced from the inspection location such that the camera focus axis and the first laser focus axis intersect an outer periphery of a glass container within the inspection location prior to intersecting when the camera focus axis and the first laser focus axis are viewed in a direction extending parallel to a container axis of rotation about which the selected glass container is rotated by the rotator.

32. The method of claim 20, wherein adjusting the position of the first laser source and the camera includes viewing a selected glass container within the inspection location and the alignment lines with an alignment camera and an alignment display operably connected to alignment camera displaying an output of the alignment camera.

33. The method of claim 21, wherein directing the multi-wavelength collimated laser beam includes, using first collimated laser beam delivery optics:

redirecting, with a second laser source redirection structure optically interposed between the second laser source and the inspection location, the second wavelength collimated laser beam produced by the second wavelength laser source along a first laser focus axis;

redirecting, with a third wavelength laser source redirection structure optically interposed between the third wavelength laser source and the inspection location, the third wavelength collimated laser beam produced by the third wavelength laser source along the first laser focus axis such that the first, second and third wavelength collimated laser beams are coincident when they intersect an outer periphery of a selected glass container within the inspection location.

34. The method of claim 33, wherein the second wavelength laser source redirection structure is made of a material that allows the first wavelength of light to pass therethrough and the second wavelength of light is reflected and the third laser source redirection structure is made of a material that allows the first and second wavelengths of light to pass therethrough and the third wavelength of light is reflected.

35. The method of claim 34, further including redirecting, with a first laser source redirection structure optically interposed between the first laser source and the inspection location, the first wavelength collimated laser beam produced by the first wavelength laser source along the first laser focus axis.

36. The method of claim 20, wherein directing the first collimated laser beam includes directing the first collimated laser beam of the first laser source along a first laser focus axis as the first collimated laser beam contacts an outer periphery of the selected glass container;
   further including:
      producing a second collimated laser beam, with a second laser source, traveling along a second laser focus axis different than the first laser focus axis;
      directing the second collimated laser beam towards the selected glass container in the inspection location at a second angle of incidence with the selected glass container being greater than or equal to a critical angle for producing internal reflection of the second collimated laser beam within the selected glass container, the second laser focus axis being at a skew angle relative to a plane normal to a container axis of rotation about which the rotator rotates the selected glass container.

37. The method of claim 36, wherein directing the second collimated laser beam directs the second collimated laser beam such that the second laser focus axis is directed to intersect an inside of an 42 of the selected glass container such that horizontal defects are detected.

38. The method of claim 20, further comprising:
   producing a second collimated laser beam with a second laser source;
   directing the second collimated laser beam towards the inspection location at an angle of incidence with the selected glass container being greater than or equal to a critical angle for producing internal reflection of the second collimated laser beam within the selected glass container;
   detecting light that escapes from the selected glass container as a result of the internally reflected second collimated laser beam intersecting a defect in the selected glass container; and
   the first and second laser sources being directed such that the internally reflected first and second collimated laser beams travel in opposite directions within the selected glass container.

* * * * *